US007049342B2

(12) United States Patent
Miyachi et al.

(10) Patent No.: US 7,049,342 B2
(45) Date of Patent: May 23, 2006

(54) SUBSTITUTED PHENYLPROPIONIC ACID DERIVATIVES

(75) Inventors: Hiroyuki Miyachi, Saitama (JP); Masahiro Nomura, Tochigi (JP); Yukie Takahashi, Fukushima (JP); Takahiro Tanase, Tochigi (JP); Kouji Murakami, Tochigi (JP); Masahiro Suzuki, Saitama (JP)

(73) Assignee: Kyorin Pharmaceutical Co., Ltd., Tokyo (JP)

(*) Notice: Subject to any disclaimer, the term of this patent is extended or adjusted under 35 U.S.C. 154(b) by 124 days.

(21) Appl. No.: 10/296,206

(22) PCT Filed: May 25, 2001

(86) PCT No.: PCT/JP01/04385

§ 371 (c)(1), (2), (4) Date: Nov. 29, 2002

(87) PCT Pub. No.: WO01/92201

PCT Pub. Date: Dec. 6, 2001

(65) Prior Publication Data

US 2003/0187068 A1 Oct. 2, 2003

(30) Foreign Application Priority Data

May 29, 2000 (JP) ............................ 2000-158424

(51) Int. Cl.
*A61K 31/195* (2006.01)
*C07C 235/52* (2006.01)

(52) U.S. Cl. ...................... 514/563; 514/562; 562/450; 562/405; 562/442; 562/443

(58) Field of Classification Search ................ 514/563, 514/562; 562/450, 405, 442, 443
See application file for complete search history.

(56) References Cited

U.S. PATENT DOCUMENTS 6,506,797 B1 1/2003 Nomura et al. ............. 514/562

FOREIGN PATENT DOCUMENTS

EP 0 930 299 8/1997
WO 97/36862 10/1997
WO 00/75103 12/2000
WO 01/25181 4/2001

OTHER PUBLICATIONS

Juan Zhang et al.: "Polyphosphoric acid catalyzed conversion of 3-(methoxyphenyl)propionic acids to derivatives of [3.3]metacyclophane-1,10-diones and 1-indanones" J. Org. Chem., vol. 58, No. 3. pp. 556-559 1993.

*Primary Examiner*—Cecilia J. Tsang
*Assistant Examiner*—Taylor Victor Oh
(74) *Attorney, Agent, or Firm*—Oblon, Spivak, McClelland, Maier & Neustadt, P.C.

(57) ABSTRACT

The invention provides novel substituted phenylpropionic acid derivatives that bind to the receptor as ligands of human peroxisome proliferator-activated receptor α (PPARα) to activate and exhibit potent lipid-decreasing action, and processes for preparing them.

It relates to substituted phenylpropionic acid derivatives represented by a general formula (1)

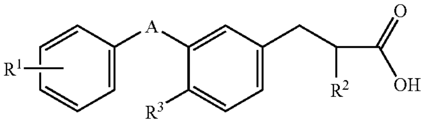

(1)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, $R^3$ denotes a lower alkoxy group with carbon atoms of 1 to 3, and the binding mode of A portion denotes $—CH_2CONH—$, $—NHCOCH_2—$, $—CH_2CH_2CO—$, $—CH_2CH_2CH_2—$, $—CH_2CH_2O—$, $—CONHCH_2—$, —CH2NHCH$_2$—, $—COCH_2O—$, $—OCH_2CO—$, $—COCH_2NH—$ or $—CHCH_2CO—$], their pharmaceutically acceptable salts and their hydrates, and processes for preparing them.

34 Claims, No Drawings

SUBSTITUTED PHENYLPROPIONIC ACID DERIVATIVES

TECHNICAL FIELD

The present invention relates to substituted phenyl-propanoic acid derivatives, effective for the therapy of abnormality of lipometabolism as agonists of human peroxisome proliferator-activated receptor (abbreviated as PPAR), in particular, as agonists for human PPARα isoform, their addition salts, processes for preparing them, and medicinal compositions containing these compounds.

BACKGROUND TECHNOLOGIES

The peroxisome proliferator-activated receptor (PPAR) is a ligand-dependent transcription factor that belongs to nuclear receptor superfamily such as steroid receptor, retinoid receptor, thyroid receptor, etc. Three isoforms (α type, β (or δ) type and γ type) with different histological distribution have been identified hitherto in human and various animal species (Proc. Natl. Acad. Sci., 1992, 89, 4653). Thereamong, the PPARα is distributed in the liver, kidney, etc. with high catabolic capacity for fatty acids and, in particular high expression is recognized in the liver (Endocrinology, 1995, 137, 354), positively or negatively controlling the expressions of genes relevant to the metabolism and the intracellular transport of fatty acids (e.g. acyl-CoA synthetic enzyme, fatty acid-binding protein and lipoprotein lipase) and apolipoprotein (AI, AII, CIII) genes relevant to the metabolisms of cholesterol and triglyceride. The PPARβ is expressed ubiquitously in the tissues of organisms, including nerve cells. At present, the physiological significance of PPARβ is unclear. The PPARγ is highly expressed in the adipocytes and involved the differentiation of adipocytes (J. Lipid Res., 1996, 37, 907). In this way, each isoform of PPAR plays specific functions in the particular organs and tissues.

Moreover, it is reported that a knock-out mouse of PPARα exhibits hypertriglyceridemia with ageing and becomes obesity mainly by increasing the white adipose tissues (J. Biol. Chem., 1998, 273, 29577), hence the relevance between activation of PPARα and decreasing action of lipids (cholesterol and triglyceride) in blood is suggested strongly.

On the other hand, fibrates and statins are widely used so far as the therapeutic drugs for hyperlipidemia. However, the fibrates have only weak decreasing effect of cholesterol, while the statins have weak decreasing effect of free fatty acids and triqlycerides. Moreover, with respect to the fibrates, various adverse effects such as gastrointestinal injury, anthema, headache, hepatic disorder, renal disorder and biliary calculus are reported. The reason is considered to be due to that the fibrates exhibit extensive pharmacological function, hence the development of a therapeutic drug for hyperlipidemia with specific mechanism is desired.

When considering the present situation of such conventional therapeutic drugs for hyperlipidemia, and the role on the adjusting mechanism of lipid metabolism and the connection to the pathology of hyperlipidemia of transcription factor called PPARα, which has become clear until now, if a compound that binds directly as a ligand of PPARα, in particular, human PPARα and is capable of activating human PPARα could be created, the medicinal use thereof would be expected as a compound that exhibits the decreasing effect of lipids (both of cholesterol and triglyceride) in blood due to very specific mechanism.

For compounds having an affinity to PPARα as ligands of PPARα, eicosanoids in HETE (hydroxyeicosatetraenoic acid) group produced via oxidation with cytochrome P-450, in particular, 8-HETE, 8-HEPE, etc. are reported in addition to LTB4 being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

On the other hand, as compounds with similar structure to the inventive substituted phenylpropanoic acid derivatives, a group of compounds shown below, etc. are reported.

As α-substituted phenylpropanoic acid derivatives with blood glucose-decreasing action and lipid-decreasing action, in Japanese Unexamined Patent Publication No. Hei 11-158144 (SS Pharmaceutical Co., Ltd.), compounds represented by a general formula (A)

(A)

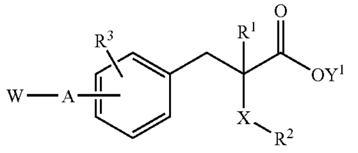

(wherein W denotes a (substituted) lactam ring, A denotes an alkylene group or alkyleneoxy group, X denotes O, S, NH or $CH_2$, $Y^1$ denotes an amino group, hydroxyl group or alkoxy group, $R^1$ denotes H, alkyl group, etc., $R^2$ denotes an alkyl group, phenyl group, etc., and R3 denotes an alkyl group, alkoxy group, etc.) are reported.

However, these compounds have different structure from that of the inventive compounds in the points that carbonyl group or amide group is not contained in A being connecting portion and that lactam ring is contained in W being end substituent, and it is not described that these compounds have the binding activity to human PPARα and the transcription-activating function.

As compounds with blood glucose-lowering action, in International Publication Number WO98/28254 (Nippon Chemiphar Co., Ltd.), compounds represented by a general formula (B)

(B)

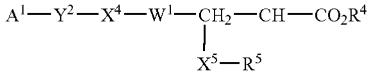

(wherein $A^1$ denotes an aryl group which may have substituents or heterocycle group, Y2 denotes an alkylene chain with carbon atoms of 1 to 5, X4 denotes bond hand, oxygen atom or sulfur atom, $W^1$ denotes a naphthalene ring which may have substituents, quinoline ring, indole ring, benzisoxazole ring or benzo[b]thiophene ring, $R^4$ denotes a hydrogen atom or alkyl group with carbon atoms of 1 to 8, $X^5$ denotes an oxygen atom or sulfur atom, and $R^5$ denotes an alkyl group with carbon atoms of 1 to 8 which may have substituents, aralkyl group or aryl group), are reported.

However, these compounds have different structure from that of the inventive compounds in the points that carbonyl group or amide group is not contained in $Y^2$ and $X^4$ being connecting portions and that $W^1$ to bind to 3-position of propionic acid is heterocycle, and it is not described that these compounds have the binding activity to human PPARα and the transcription-activating function.

As propanoic acid derivatives with blood glucose-lowering action and lipid-decreasing action, in International Publication Number WO98/07699 (Japan Tobacco Inc.), compounds represented by a general formula (C)

(C)

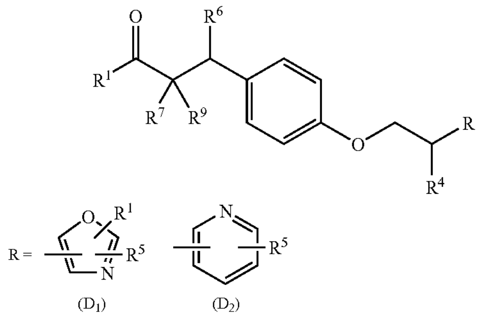

(wherein R denotes a substituent represented by $D_1$ or $D_2$, $R^1$ denotes an aromatic ring, cycloalkyl group or heteroaromatic ring, $R^5$ denotes an alkyl group, $R^4$ denotes a hydrogen atom or alkyl group, $R^6$ denotes a hydrogen atom or it may be connected to $R^9$ to form double bond, $R^7$ denotes a carboxyl group, acyl group, alkoxycarbonyl group which may have substituents, alkyl group, aryloxycarbonyl group, aralkyloxycarbonyl group, carbamoyl group, $NHR^8$ group or $OR^8$ group, $R^8$ denotes an acyl group which may have substituents or alkoxycarbonyl group, $R^9$ denotes a hydrogen atom, alkyl group or alkoxycarbonyl group, and $R^{10}$ denotes a hydrogen atom, amino group, alkoxy group, alkyl group, aryloxy group or aralkyloxy group), are reported.

However, these compounds also have different structure from that of the inventive compounds in the point that substituents on. benzene ring are of disubstituted form at 1-position and 4-position, and it is not described that these compounds have the binding activity to human PPARα and the transcription-activating function.

As carboxylic acid derivatives with working function on leukotriene receptor, in Japanese Unexamined Patent Publication No. Sho 63-91354 (Yamanouchi Pharmaceutical Co., Ltd.), compounds represented by a general formula (E)

(E)

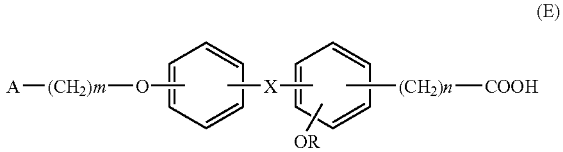

(wherein A denotes a hydrogen atom or phenyl group, m denotes an integer of 3 to 10, n denotes an integer of 1 to 6, X denotes CONH group or NHCO group, and R denotes a carboxy lower alkyl group or carboxy lower alkylcarbamoyl group (however, when A is phenyl group, R is carboxy lower alkylcarbamoyl lower alkyl group)), are reported.

However, since these compounds have no substituent at 2-position of propanoic acid and carbonyl groups exist in all of R group portions, the structure differs from that of the inventive compounds, and it is not described that these compounds have the binding activity to human PPARα and the transcription-activating function.

As carboxylic acid derivatives with antagonism against fibrinogen receptor, in U.S. Pat. No. 5,227,490 (Merck & Co., Inc.), compounds represented by a general formula (F)

(F)

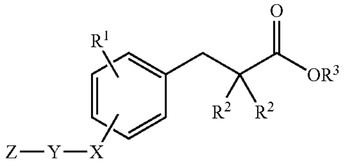

(wherein $R^1$ denotes a hydrogen atom, $C_{1-6}$ alkyl group, aryl $C_{4-10}$ alkyl group, aryl group, carboxyl group, $C_{1-6}$ alkoxy group, carboxy $C_{0-6}$ alkyl group, carboxy $C_{0-6}$ alkoxy group, hydroxy $C_{1-6}$ alkyl group, $C_{1-4}$ alkylsulfonyl $C_{0-6}$ alkyl group, $C_{0-4}$ alkylamino $C_{0-6}$ alkyl group, aryl $C_{0-10}$ alkylamino $C_{0-6}$ alkyl group, $C_{2-10}$ acylamino $C_{0-6}$ alkyl group, $C_{1-4}$ carboalkoxy $C_{0-6}$ alkyl group or halogen atom, $R^2$s denote identically or differently hydrogen atoms, halogen atoms, hydroxyl groups, $C_{1-6}$ alkoxy groups, aryl $C_{0-4}$ alkyl groups, aryl $C_{0-6}$ alkoxy groups or $C_{1-6}$ alkyl groups which may have substituents, $R^3$ denotes a hydrogen atom, $C_{1-6}$ alkyl group or aryl $C_{1-10}$ alkyl group, X denotes an oxygen atom, sulfur atom, SO group, $SO_2$ group, CO group, $NR^4CO$ group, $CONR^4$ group, $CH_2$ group, CH═CH group or $NR^4CS$ group, Y denotes a $C_{1-10}$ alkyl group which is unsubstituted or which may have substituents, $C_{4-8}$ cycloalkyl group, aryl group, $C_{0-3}$ alkylaryl $C_{0-3}$ alkyl group, $C_{0-3}$ alkylaryl $C_{0-3}$ alkylcarbonyl group, $C_{0-3}$ alkylaryl $C_{0-3}$ alkylcarboxyamide group, $C_{0-3}$ alkylaryloxy $C_{0-3}$ alkyl group, CONH group, NHCO group or $(CH_2)m$-Q-$(CH_2)n$ group (however, Q denotes a $C_{3-8}$ membered heterocycle containing 1 to 3 kinds of heteroatoms selected from oxygen and sulfur, and m and n denote 0 to 4), and Z denotes a $NR^4R^5$ group (however, $R^4$ and $R^5$ denote identically or differently hydrogen atoms, $C_{1-6}$ alkyl groups, aryl $C_{1-10}$ alkyl groups in which alkyl group is unsubstituted or may be substituted with $C_{1-4}$ alkoxy group, carboxy $C_{0-6}$ alkyl group, hydroxyl group, halogen atom, or 4–9 membered monocyclic or bicyclic ring containing 1 to 3 heteroatoms selected from nitrogen, oxygen and sulfur) or guanidino group which may have substituents), are reported.

However, from the fact that these compounds are amino acid derivatives inevitably containing amino group which may have substituents, in all of Z group portions, the structure is different from that of the inventive compounds, and it is not described that these compounds have the binding activity to human PPARα and the transcription-activating function.

With respect to patents that report the working function on PPAR α, compounds represented by a general formula (G)

(G)

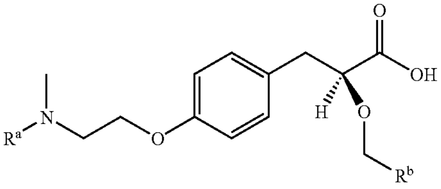

(wherein $R^a$ denotes a 2-benzoxazolyl group or 2-pyridyl group, and $R^b$ denotes a methoxymethyl group or trifluoromethyl group), are reported in International Open Number WO97/25042 (SmithKline Beecham plc.) as compounds with working functions on PPARα and PPARγ. However, the structure of these compounds is different from that of the inventive compounds in the point that substituents on benzene ring are of disubstituted derivatives at 1-position and 4-position, and further it is not described that they have the binding activity to human PPARα and the transcription-activating function.

As compounds with working function on PPARα, in International Publication Number WO97/36579 (Glaxo Welcome Corp.), compounds represented by a general formula (H)

(H)

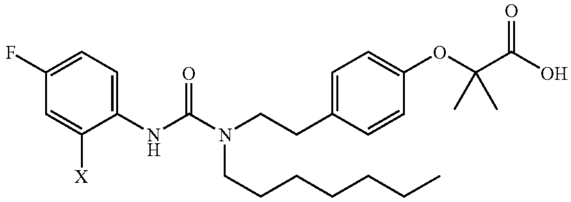

(wherein X denotes a hydrogen atom or fluorine atom), are reported.

However, the structure is different from that of the inventive compounds in the points that these compounds are phenoxyacetic acid derivatives and that the position relationship of substituents on benzene ring is of disubstituted form at 1-position and 4-position. Also, the transcription-activating function of PPARα is never satisfied in strength.

The hyperlipidemia is a risk factor of arterial sclerosis and, from a viewpoint of the prevention of arteriosclerotic diseases, in particular, coronary arteriosclerotic disease, the development of a therapeutic drug for hyperlipidemia with effectiveness and high safety is desired clinically.

DISCLOSURE OF THE INVENTION

As a result of diligent studies paying an attention to such specific role on the lipid metabolism of human PPARα, aiming at the creation of structurally novel drug with effectiveness and high safety as a therapeutic drug for hyperlipidemia, the inventors have found that novel substituted phenylpropanoic acid derivatives represented by a following general formula (1) have excellent binding activity to human PPARα and transcriptional activation and exhibit the lipid-decreasing action of lipids (cholesterol and triglyceride) in blood, leading to the completion of the invention.

Namely, the invention relates to substituted phenylpropanoic acid derivatives represented by a general formula (1)

(1)

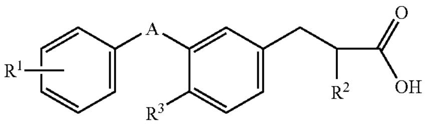

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, $R^3$ denotes a lower alkoxy group with carbon atoms of 1 to 3, and the binding mode of A portion denotes $-CH_2CONH-$, $-NHCOCH_2-$, $-CH_2CH_2CO-$, $-CH_2CH_2CH_2-$, $-CH_2CH_2O-$, $-CONHCH_2-$, $-CH_2NHCH_2-$, $-COCH_2O-$, $-OCH_2CO-$, $-COCH_2NH-$ or $-NHCH_{2C}O-$), their pharmaceutically acceptable salts and their hydrates.

The salts of the compounds represented by the general formula (1) in the invention are of common use and metal salts, for example, alkali metal salts (e.g. sodium salt, potassium salt, lithium salt, etc.), alkaline earth metal salts (e.g. calcium salt, magnesium salt, etc.), aluminum salt, and other pharmacologically acceptable salts are mentioned. Moreover, in the compounds represented by the general formula (1) in the invention, compounds capable of making acid addition salts can exist. As the acids in this case, pharmacologically acceptable inorganic acids, for example, hydrochloric acid, sulfuric acid, hydrobromic acid and phosphoric acid, and organic acids, for example, maleic acid, fumaric acid, acetic acid, oxalic acid, tartaric acid and benzenesulfonic acid, and the like are mentioned.

Moreover, the compounds represented by the general formula (1) in the invention sometimes include optical isomers based on the propanoic acid portion. Furthermore, compounds obtainable in the process of synthesizing the compounds represented by the general formula (1) sometimes include a mixture of geometrical isomers. Such isomers and their mixtures are all included in the scope of the invention.

Respective optical isomers can be prepared through stereoselective synthetic process. Moreover, they can also be prepared by separating diastereomeric ester derivatives or oxazolidinone derivatives obtainable by reacting with optically active alcohol derivatives or optically active oxazolidinone derivatives by a technique of fractional crystallization or chromatography, followed by hydrolysis. Furthermore, they can also be prepared by a technique of chromatography that uses chiral support.

In the general formula (1) of the invention, for "lower alkyl group with carbon atoms of 1 to 4", straight chain or branched ones with carbon atoms of 1 to 4 such as methyl, ethyl, propyl, isopropyl and butyl are mentioned.

For "lower alkoxy group with carbon atoms of 1 to 3", straight chain or branched ones with carbon atoms of 1 to 3 such as methoxy, ethoxy, isopropoxy and propoxy are mentioned.

For "halogen atoms", fluorine atom, chlorine atom, bromine atom and iodine atom are mentioned.

For substituents acceptable in "phenyl group which is unsubstituted or may have substituents, phenoxy group which is unsubstituted or may have substituents or benzyloxy group which is unsubstituted or may have substituents", lower alkyl group with carbon atoms of 1 to 4, lower alkoxy group with carbon atoms of 1 to 3, halogen atom, etc. are mentioned.

According to the invention, compounds of a general formula (1b), the binding mode of A portion being $-CH_2CONH-$, in the compounds of said general formula (1) can be prepared, for example, through following processes (Scheme 1).

Scheme 1

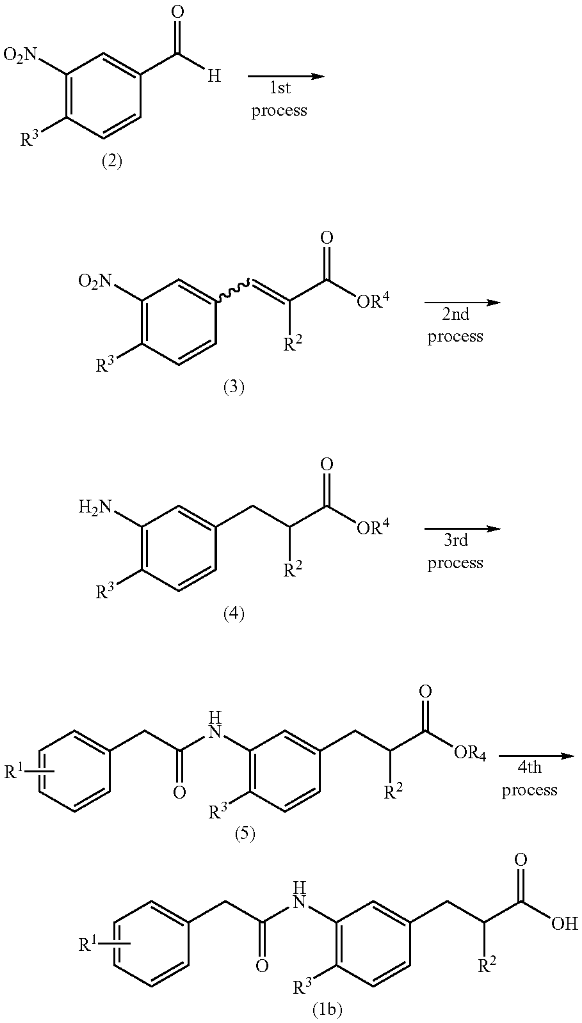

(2) (3) (4) (5) (1b)

Namely, compounds represented by the general formula (1b)

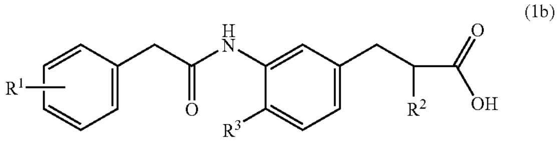

(1b)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], can be prepared by reacting (Wittig reaction or Horner-Emmons reaction; first process) compounds represented by a general formula (2)

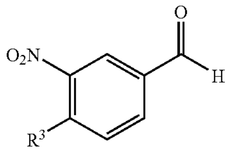

(2)

[wherein $R^3$ denotes a lower alkoxy group with carbon atoms of 1 to 3], with compounds represented by a general formula (6)

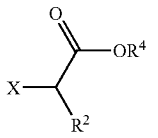

(6)

[wherein $R^2$ is as described above, $R^4$ is a lower alkyl group with carbon atoms of 1 to 4, and X denotes a $PPh_3$ group or $PO(OC_2H_5)_2$ group], in the presence of base, to synthesize compounds represented by a general formula (3)

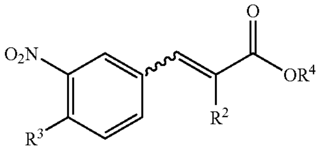

(3)

[wherein $R^2$, $R^3$ and $R^4$ are as described above], by reducing and hydrogenolyzing (second process) these compounds, to obtain compounds represented by a general formula (4)

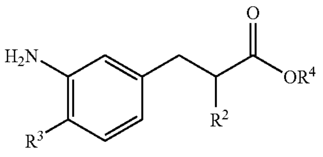

(4)

[wherein $R^2$, $R^3$ and $R^4$ are as described above], by reacting (third process) these compounds with compounds represented by a general formula (7)

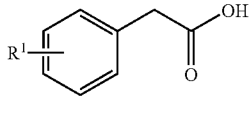

(7)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituentsis], to obtain compounds represented by a general formula (5)

(5)

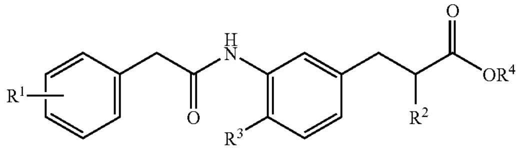

[wherein $R^1$, $R^2$, $R^3$ and $R^4$ are as described above]. and by hydrolyzing (fourth process) $COOR^4$ position of these compounds.

In the reaction of the first process, as a base, for example, alkali metal hydride such as sodium hydride, organometallic compound such as butyl lithium, metal amide such as lithium diisopropylamide, or metal alkoxide such as sodium methoxide or potassium t-butoxide can be used in a solvent such as tetrahydrofuran, toluene, dioxane or N,N-dimethylformamide. The reaction can be performed at a reaction temperature of −20° C. to 150° C., preferably 0° C. to 50° C.

The reduction reaction of the second process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

The condensation reaction of the third process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using reactive-derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The hydrolysis reaction of the fourth process can be performed under alkaline condition. For the alkaline condition, lithium hydroxide, sodium hydroxide, potassium hydroxide or the like is used. The reaction can be performed at a reaction temperature of 0° C. to 80° C., preferably room temperature to 60° C.

Moreover, according to the invention, compounds of the general formula (1b), the binding mode of A portion being $—CH_2CONH—$, in the compounds of said general formula (1) can be prepared, for example, through following processes (Scheme 2).

Scheme 2

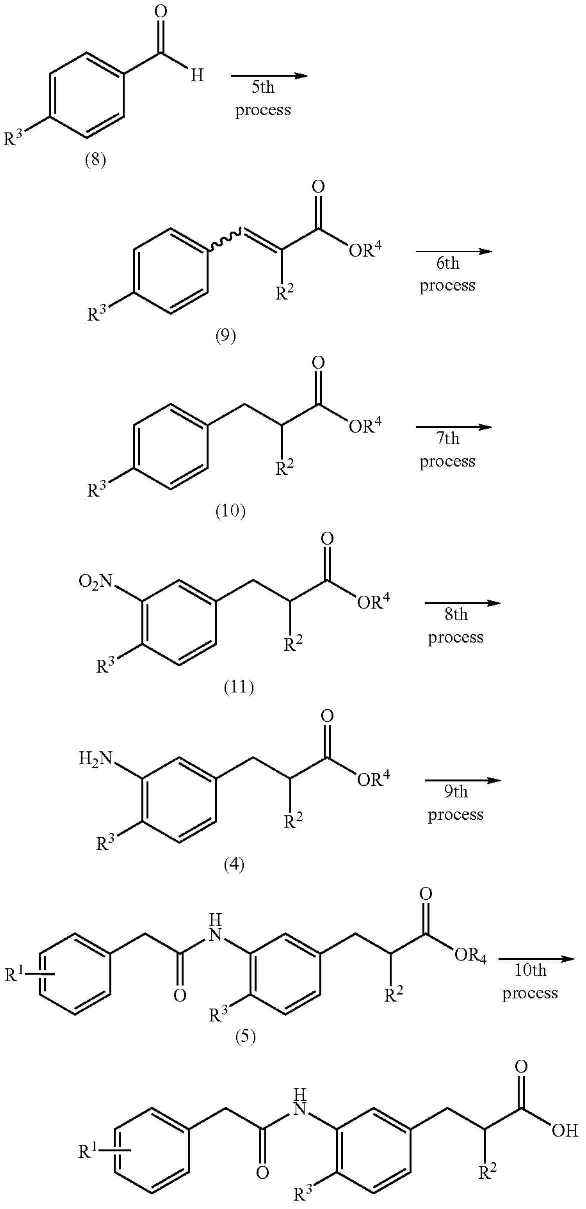

(8)

(9)

(10)

(11)

(4)

(5)

Namely, compounds represented by the general formula (1b)

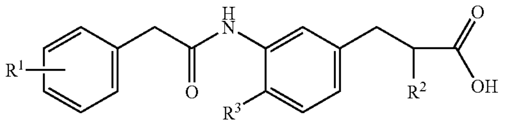

(1b)

[wherein $R^1$ denotes a lower alkyl group with carbon atoms of 1 to 4, lower alkoxy group with carbon atoms of 1 to 3, tri-fluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], can be prepared by reacting (fifth process) compounds represented by a general formula (8)

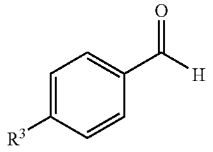

(8)

[wherein $R^3$ denotes a lower alkoxy group with carbon atoms of 1 to 3], with compounds represented by the general formula (6)

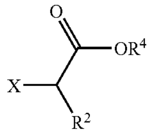

(6)

[wherein $R^2$ is as described above, $R^4$ is a lower alkyl group with carbon atoms of 1 to 4, and X denotes $PPh_3$ or $PO(OC_2H_5)_2$], in the presence of base, to synthesize compounds represented by a general formula (9)

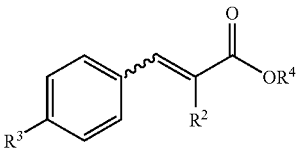

(9)

[wherein $R^2$, $R^3$ and $R^4$ are as described above], by reducing (sixth process) these compounds, to synthesize compounds represented by a general formula (10)

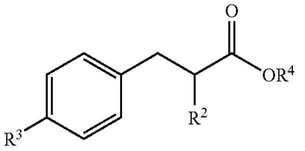

(10)

[wherein $R^2$, $R^3$ and $R^4$ are as described above], by nitrating (seventh process) these compounds to synthesize compounds represented by a general formula (11)

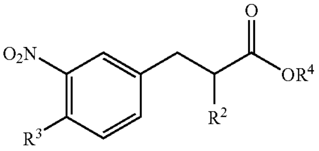

(11)

[wherein $R^2$, $R^3$ and $R^4$ are as described above], by reducing these compounds to synthesize compounds represented by the general formula (4)

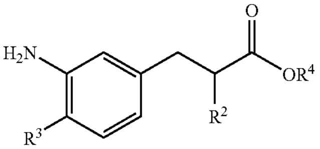

(4)

[wherein $R^2$, $R^3$ and $R^4$ are as described above], by reacting these compounds with compounds represented by the general formula (7)

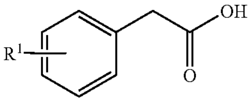

(7)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents], to synthesize compounds represented by the general formula (5)

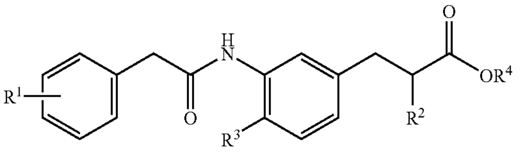

(5)

[wherein $R^1$, $R^2$, $R^3$ and $R^4$ are as described above], and by hydrolyzing (tenth process) $COOR^4$ portion of these compounds.

In the reaction of the fifth process, as a base, for example, alkali metal hydride such as sodium hydride, organometallic compound such as butyl lithium, metal amide such as lithium diisopropylamide, or metal alkoxide such as sodium methoxide or potassium t-butoxide can be used in a solvent such as tetrahydrofuran, toluene, dioxane or N,N-dimethylformamide. The reaction can be performed at a reaction temperature of −20° C. to 150° C., preferably 0° C. to 50° C.

The reaction of the sixth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

The reaction of the seventh process can be performed in nitric acid or a mixed solvent such as nitric acid and sulfuric acid or nitric acid and acetic anhydride. The reaction can be implemented at a reaction temperature of −20° C. to 150° C., preferably 0° C. to 100° C.

The reduction reaction of the eighth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

The condensation reaction of the ninth process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The hydrolysis reaction of the tenth process can be performed under alkaline condition. For the alkaline condition, lithium hydroxide, sodium hydroxide, potassium hydroxide or the like is used. The reaction can be performed at a reaction temperature of 0° C. to 80° C., preferably room temperature to 60° C.

Next, compounds of a general formula (1c), the binding mode of A portion being $-NHCOCH_2-$, in the compounds of said general formula (1) of the invention can be prepared through following processes (Scheme 3).

Scheme 3

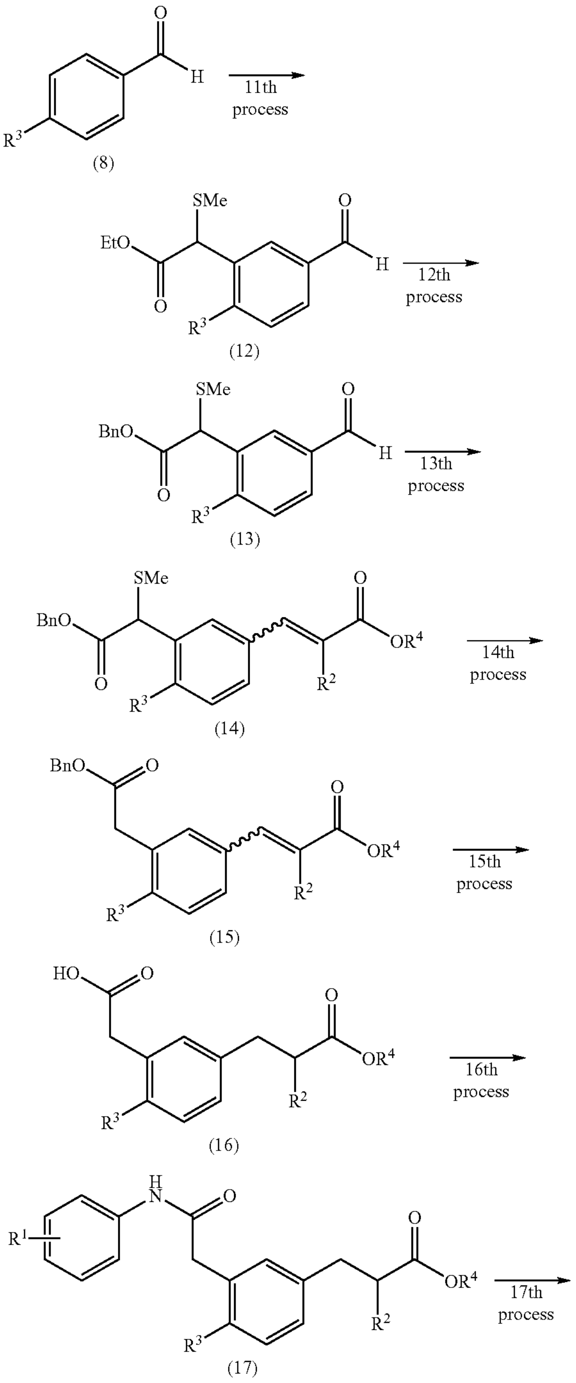

(8) (12) (13) (14) (15) (16) (17)

-continued

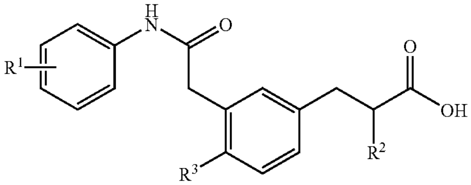

(1c)

Namely, compounds represented by the general formula (1c)

(1c)

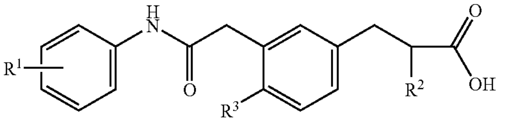

[wherein $R^1$ denotes a lower alkyl group with carbon atoms of 1 to 4, lower alkoxy group with carbon atoms of 1 to 3, tri-fluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], can be prepared by reacting (eleventh process) compounds represented by the general formula (8)

(8)

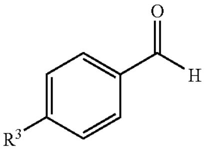

[wherein $R^3$ denotes a lower alkoxy group with carbon atoms of 1 to 3], with known ethyl 2-chloro-2-methylthioacetate (e.g. Chem. Pharm. Bull., 1982, 30, 915), to synthesize compounds represented by a general formula (12)

(12)

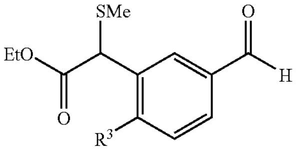

[wherein $R^3$ is as described above], by hydrolyzing these compounds and then reacting (twelfth process) carboxylic acid derivatives obtained with benzyl bromide, to synthesize compounds represented by a general formula (13)

(13)

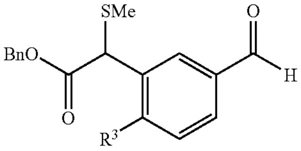

[wherein $R^3$ is as described above], by reacting (thirteenth process) these compounds with compounds represented by the general formula (6)

(6)

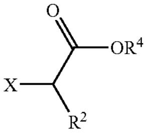

[wherein $R^2$ is as described above, $R^4$ denotes a lower alkyl group with carbon atoms of 1 to 4, and X denotes $PPh_3$ or $PO(OC_2H_5)_2$], in the presence of base, to synthesize compounds represented by a general formula (14)

(14)

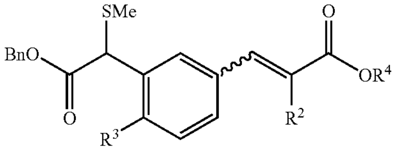

[wherein $R^2$, $R^3$ and $R^4$ are as described above], by removing (fourteenth process) methylthio group of these compounds, to synthesize compounds represented by a general formula (15)

(15)

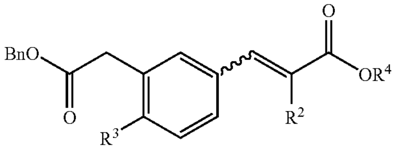

[wherein $R^2$, $R^3$ and $R^4$ are as described above], by reducing and hydrogenating (fifteenth process) these compounds, to synthesize compounds represented by a general formula (16)

(16)

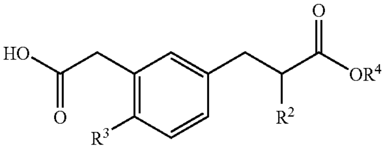

[wherein $R^2$, $R^3$ and $R^4$ are as described above], by reacting (sixteenth process) these compounds with compounds represented by a general formula (18)

(18)

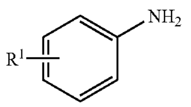

[wherein $R^1$ denotes a lower alkyl group with carbon atoms of 1 to 4, lower alkoxy group with carbon atoms of 1 to 3, tri-fluoromethyl group, trifluoromethoxy group, phenyl group which is unsubstituted or may have substituents, phenoxy group which is unsubstituted or may have substituents or benzyloxy group which is unsubstituted or may have substituents], to synthesize compounds represented by a general formula (17)

(17)

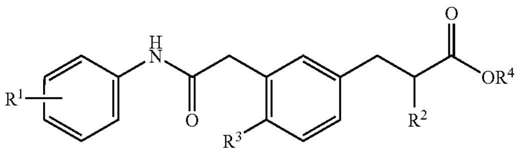

[wherein $R^1$, $R^2$, $R^3$ and $R^4$ are as described above], and by hydrolyzing (seventeenth process) $COOR^4$ portion of these compounds.

The reaction of the eleventh process can be performed in a solvent such as methylene chloride, chloroform or nitrobenzene. As a Lewis acid, aluminum chloride, tin chloride, boron trifluoride or the like can be used. The reaction can be performed at a reaction temperature of −20° C. to 150° C., preferably refluxing temperature of solvent.

In the reaction of the twelfth process, first, the hydrolysis reaction can be performed under alkaline condition. For the alkaline condition, lithium hydroxide, sodium hydroxide, potassium hydroxide or the like is used. The reaction can be performed at a reaction temperature of 0° C. to 80° C., preferably room temperature to 60° C. Next benzyl esterification reaction can be performed in a solvent such as dioxane, N,N-dimethylformamide or dimethyl sulfoxide in the presence or absence of, for example, alkali metal hydride such as sodium hydride, alkali metal hydroxide such as sodium hydroxide, alkali metal carbonate such as potassium carbonate, or organic base such as pyridine or triethylamine as a base. The reaction can be performed at a reaction temperature of 0° C. to 150° C., preferably room temperature to 60° C.

In the reaction of the thirteenth process, as a base, for example, alkali metal hydride such as sodium hydride, organometallic compound such as butyl lithium, metal amide such as lithium diisopropylamide, or metal alkoxide such as sodium methoxide or potassium t-butoxide can be used in a solvent such as tetrahydrofuran, toluene, dioxane or N,N-dimethylformamide. The reaction can be performed at a reaction temperature of −20° C. to 150° C., preferably 0° C. to 50° C.

The reaction of the fourteenth process can be performed in a solvent such as acetic acid or hydrochloric acid by reacting metallic zinc, zinc amalgam or zinc-copper alloy. The reaction can be performed at a reaction temperature of −10° C. to 100° C., preferably 0° C. to room temperature.

The reduction reaction of the fifteenth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

The condensation reaction of the sixteenth process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The hydrolysis reaction of the seventeenth process can be performed under alkaline condition. For the alkaline condition, lithium hydroxide, sodium hydroxide, potassium hydroxide or the like is used. The reaction can be performed at a reaction temperature of 0° C. to 80° C., preferably room temperature to 60° C.

Moreover, according to the invention, compounds of general formulae (1d) and (1e), the binding modes of A portion being $—CH_2CH_2CO—$ and $—CH_2CH_2CH_2$', in the compounds of said general formula (1) can be prepared, for example, through following processes (Scheme 4).

Scheme 4

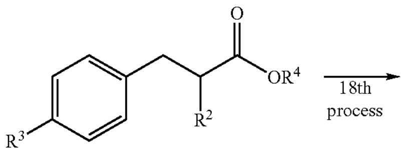

(10)

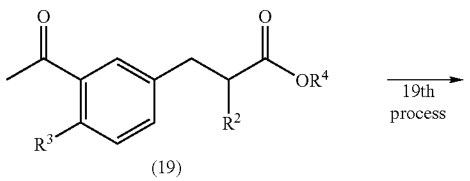

(19)

-continued

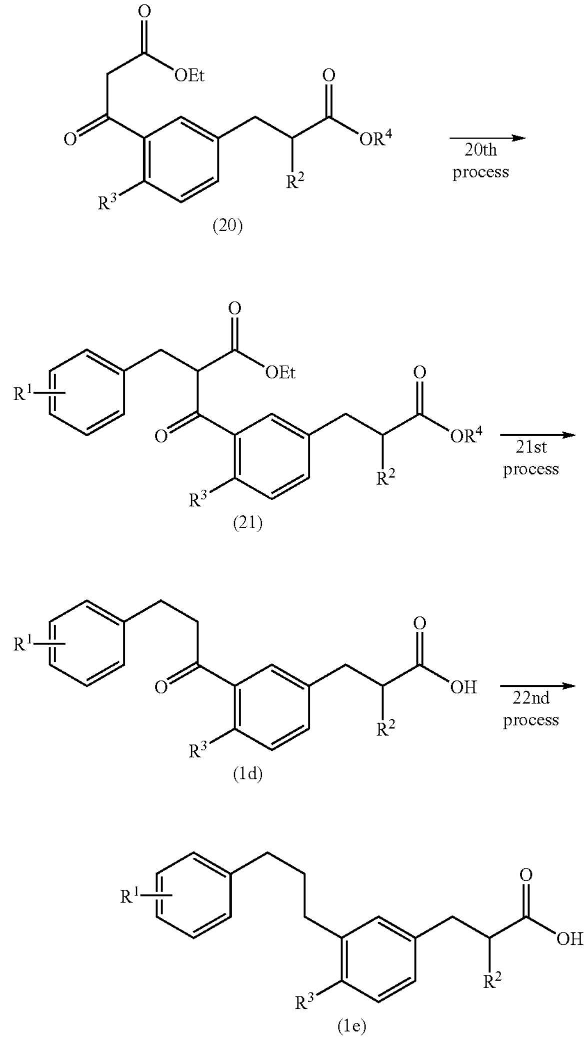

Namely, compounds represented by the general formula (1d)

(1d)

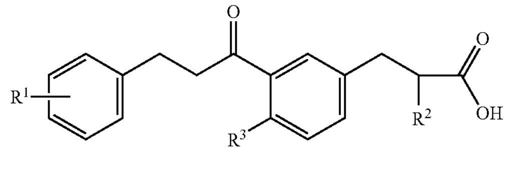

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], and compounds represented by the general formula (1e)

(1e)

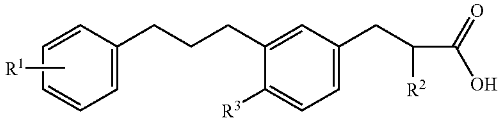

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], can be prepared by reacting (eighteenth process) compounds represented by the general formula (10)

(10)

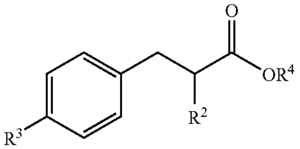

[wherein $R^2$ denotes a hydrogen atom, lower alkyl group with carbon atoms of 1 to 4 or lower alkoxy group with carbon atoms of 1 to 3, $R^3$ denotes a lower alkoxy group with carbon atoms of 1 to 3, and $R^4$ denotes a lower alkyl group with carbon atoms of 1 to 4], with acetyl chloride in the presence of Lewis acid, to synthesize compounds represented by a general formula (19)

(19)

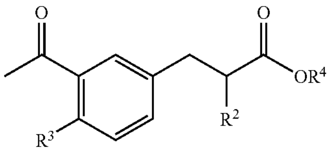

[wherein $R^2$, $R^3$ and $R^4$ are as described above], by reacting (nineteenth process) these compounds with diethyl carbonate in the presence of base, to synthesize compounds represented by a general formula (20)

(20)

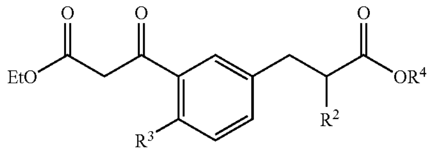

[wherein $R^2$, $R^3$ and $R^4$ are as described above], by reacting (twentieth process) these compounds with compounds represented by a general formula (22)

(22)

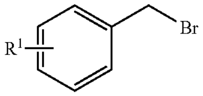

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents], in the presence of base, to synthesize compounds represented by a general formula (21)

(21)

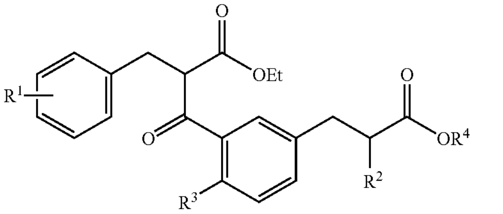

[wherein $R^1$, $R^2$, $R^3$ and $R^4$ are as described above], and by hydrolyzing and decarboxylating (twenty-first process) these compounds, thereby preparing compounds represented by the general formula (1d), and further, by hydrogenating (twenty-second process) compounds represented by the general formula (1d), thereby preparing compounds represented by the general formula (1e).

The reaction of the eighteenth process can be performed in a solvent such as methylene chloride, chloroform or nitrobenzene. As a Lewis acid, aluminum chloride, tin chloride, boron trifluoride or the like can be used. The reaction can be performed at a reaction temperature of −20° C. to 150° C., preferably 0° C. to refluxing temperature of solvent.

In the reaction of the nineteenth process, as a base, for example, alkali metal hydride such as sodium hydride, organo-metallic-compound such as butyl lithium, metal amide such as lithium diisopropylamide, or metal alkoxide such as sodium methoxide or potassium t-butoxide can be used in a solvent such as tetrahydrofuran, toluene, dioxane, ethanol or N,N-dimethylformamide, or a mixed solvent thereof. The reaction can be performed at a reaction temperature of −20° C. to 150° C., preferably 0° C. to refluxing temperature of solvent.

In the reaction of the twentieth process, as a base, for example, alkali metal hydride such as sodium hydride, organometallic compound such as butyl lithium, metal amide such as lithium diisopropylamide, or metal alkoxide such as sodium methoxide or potassium t-butoxide can be used in a solvent such as tetrahydrofuran, toluene, dioxane or N,N-dimethylformamide. The reaction can be performed at a reaction temperature of −20° C. to 150° C., preferably 0° C. to refluxing temperature of solvent.

The reaction of the twenty-first process can be performed in a solvent such as acetic acid, hydrochloric acid or sulfuric acid, or a mixed solvent thereof, or a mixed solvent with organic solvent such as ethanol. The reaction can be performed at a reaction temperature of room temperature to 150° C.

The reduction reaction of the twenty-second process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

Moreover, according to the invention, compounds of general formula (1f), the binding mode of A portion being —$CH_2CH_2O$—, in the compounds of said general formula (1) can be prepared, for example, through following processes (Scheme 5).

Scheme 5

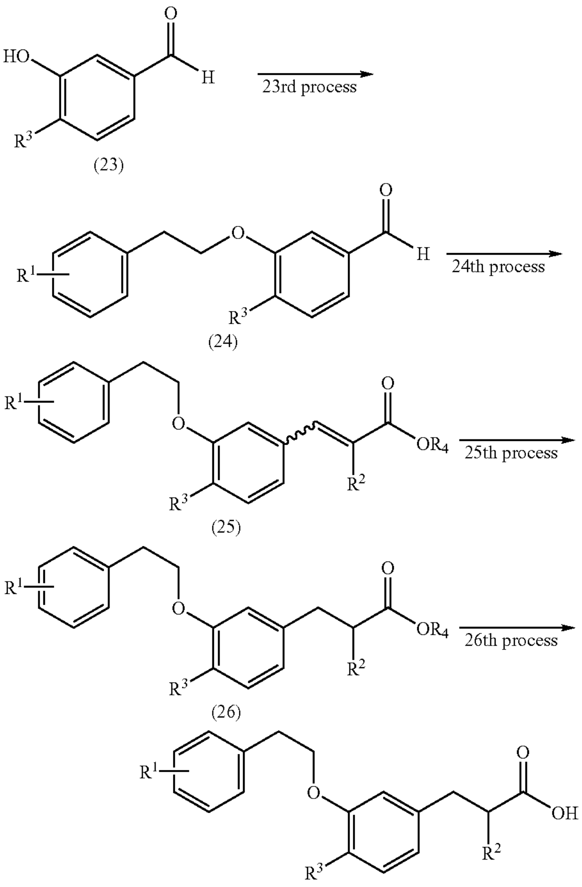

(23) (24) (25) (26) (1f)

Namely, compounds represented by the general formula (1f)

(1f)

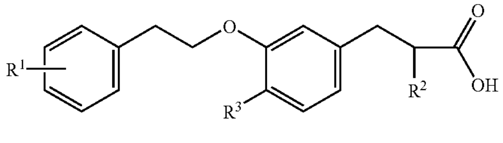

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], can be prepared by reacting (twenty-third process) compounds represented by a general formula (23)

(23)

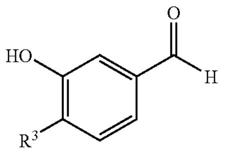

[wherein $R^3$ denotes a lower alkoxy group with carbon atoms of 1 to 3], with compounds represented by a general formula (27)

(27)

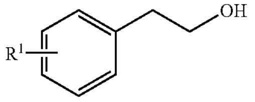

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents], to synthesize compounds represented by a general formula (24)

(24)

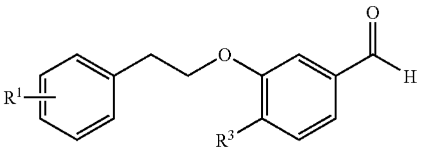

[wherein $R^1$ and $R^3$ are as described above], by reacting (twenty-fourth process) these compounds with compounds represented by the general formula (6)

(6)

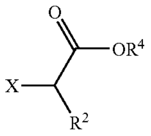

[wherein $R^2$ is as described above, $R^4$ denotes a lower alkyl group with carbon atoms of 1 to 4, and X denotes $PPh_3$ or $PO(OC_2H_5)_2$], in the presence of base, to synthesize compounds represented by a general formula (25)

(25)

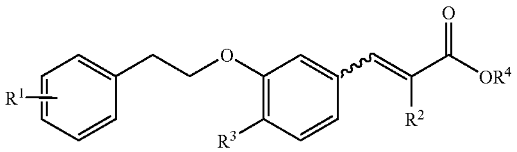

[wherein $R^1$, $R^2$, $R^3$ and $R^4$ are as described above], by reducing (twenty-fifth process) the double bond of these compounds, to synthesize compounds represented by a general formula (26)

(26)

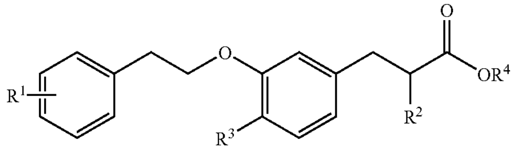

[wherein $R^1$, $R^2$, $R^3$ and $R^4$ are as described above], and by hydrolyzing (twenty-sixth process) $COOR^4$ portion of these compounds.

The reaction of the twenty-third process can be performed in a solvent such as ether, tetrahydrofuran, dioxane, benzene or toluene, in the presence of base, triphenylphosphine, tri(o-tolylphosphine) and diethyl azodicarboxylate or diisopropyl azodicarboxylate (Mitsunobu reaction). The reaction can be performed at a reaction temperature of −20° C. to 150° C., preferably 0° C. to 100° C.

The reaction of the twenty-fourth process can be performed in a solvent such as ether, tetrahydrofuran or dioxane in the presence of base. As the base, for example, alkali metal hydride such as sodium hydride, organometallic compound such as butyl lithium, metal amide such as lithium diisopropylamide, or metal alkoxide such as sodium methoxide or potassium t-butoxide can be used. The reaction can be performed at a reaction temperature of −20° C. to 150° C., preferably 0° C. to 50° C.

The reaction of the twenty-fifth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

The hydrolysis reaction of the twenty-sixth process can be implemented under alkaline condition. For the alkaline condition, lithium hydroxide, sodium hydroxide, potassium hydroxide or the like is used. The reaction can be implemented at a reaction temperature of 0° C. to 80° C., preferably room temperature to 60° C.

Moreover, according to the invention, compounds of general formulae (1g) and (1h), the binding modes of A portion being $-CH_2NHCH_2-$ and $-CONHCH_2-$, in the compounds of said general formula (1) can be prepared, for example, through following processes (Scheme 6).

Scheme 6

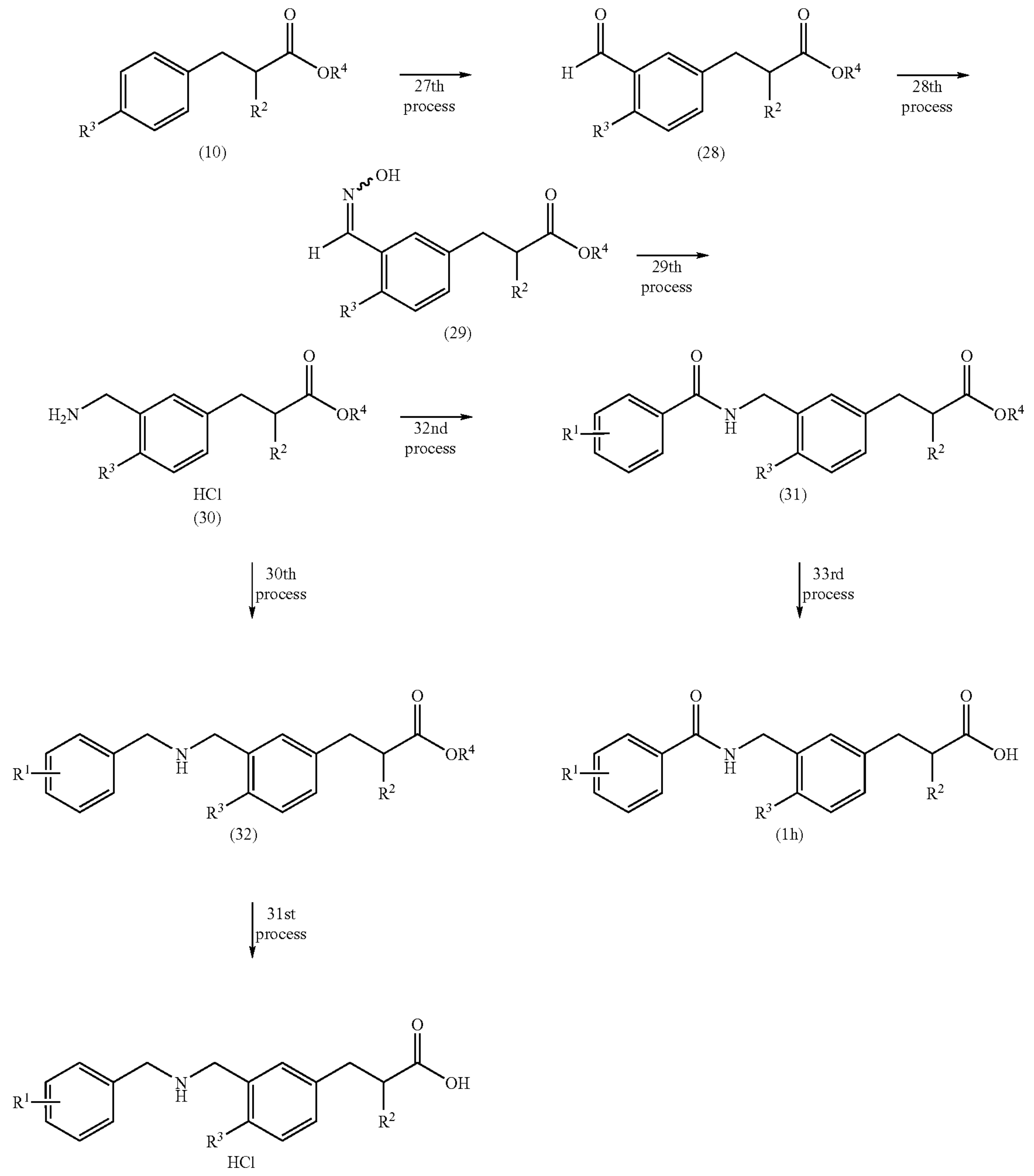

(10) (28) (29) HCl (30) (31) (32) (1h) HCl (1g)

Namely, compounds represented by the general formula (1g)

(1g)

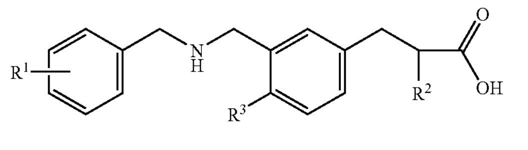

HCl

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], can be prepared by reacting (twenty-seventh process) compounds represented by the general formula (10)

(10)

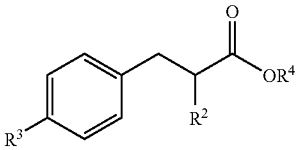

[wherein $R^2$ denotes a hydrogen atom, lower alkyl group with carbon atoms of 1 to 4 or lower alkoxy group with carbon atoms of 1 to 3, $R^3$ denotes a lower alkoxy group with carbon atoms of 1 to 3, and $R^4$ denotes a lower alkyl group with carbon atoms of 1 to 4], with chloromethyl methyl ether in the presence of Lewis acid, to synthesize compounds represented by a general formula (28)

(28)

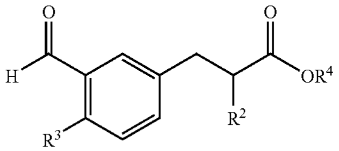

[wherein $R^2$ denotes a lower alkyl group with carbon atoms of 1 to 4, trifluoroethyl group or lower alkoxy group with carbon atoms of 1 to 3, $R^3$ denotes a lower alkoxy group with carbon atoms of 1 to 3, and $R^4$ denotes a lower alkyl group with carbon atoms of 1 to 4], by reacting (twenty-eighth process) these compounds with hydroxylamine, to synthesize compounds represented by a general formula (29)

(29)

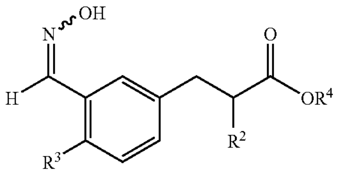

[wherein $R^2$, $R^3$ and $R^4$ are as described above], by reducing (twenty-ninth process) these compounds to synthesize compounds represented by a general formula (30)

(30)

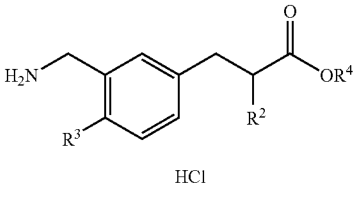

[wherein $R^2$, $R^3$ and $R^4$ are as described above], by reacting (thirtieth process) these compounds with compounds represented by the general formula (22)

(22)

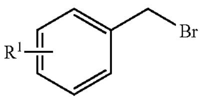

[wherein $R^1$ is as described above], to synthesize compounds represented by a general formula (32)

(32)

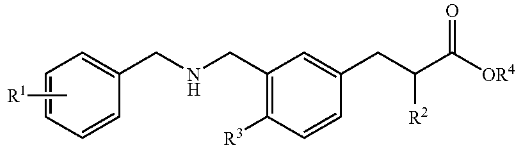

[wherein $R^1$, $R^2$, $R^3$ and $R^4$ are as described above], and by hydrolyzing (thirty-first process) $COOR^4$ portion of these compounds.

Moreover, compounds represented by the general formula (1h)

(1h)

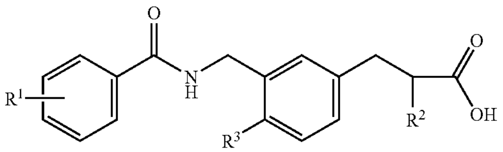

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and R3 denotes a lower alkoxy group with carbon atoms of 1 to 3], can be prepared by reacting (thirty-second process) compounds represented by the general formula (30)

(30)

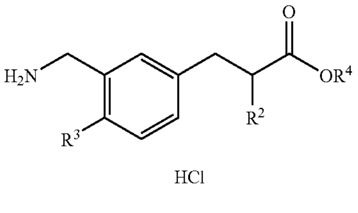

[wherein $R^2$, $R^3$ and $R^4$ are as described above], with compounds represented by a general formula (33)

(33)

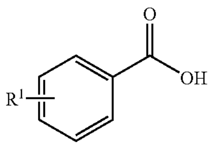

[wherein $R^1$ denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy.group which is unsubstituted or may have substituents], to synthesize compounds represented by a general formula (31)

(31)

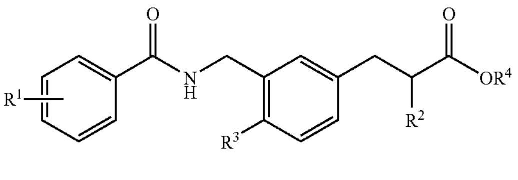

[wherein $R^1$, $R^2$, $R^3$ and $R^4$ are as described above], and by hydrolyzing (thirty-third process) $COOR^4$ portion of these compounds.

The reaction of the twenty-seventh process can be performed in a solvent such as methylene chloride, chloroform or nitrobenzene. As a Lewis acid, aluminum chloride, tin chloride, boron trifluoride, titanium tetrachloride or the like can be used. The reaction can be performed at a reaction temperature of −50° C. to 150° C., preferably −20° C. to refluxing temperature of solvent.

The reaction of the twenty-eighth process can be performed in a solvent such as methanol, ethanol, tetrahydrofuran or dioxane in the presence of base of alkali metal hydroxide such as sodium hydroxide, alkali metal carbonate such as potassium carbonate, organic base such as pyridine, or the like. The reaction can be performed at a reaction temperature of −20° C. to 150° C., preferably 0° C. to 100° C.

The reaction of the twenty-ninth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina and in the presence or absence of acid such as hydrochloric acid or acetic acid. The reaction can be performed at a reaction temperature of 0° C. to 100° C., preferably room temperature to 80° C.

In the reaction of the thirtieth process, as a base, for example, alkali metal hydroxide such as sodium hydroxide, alkali metal carbonate such as potassium carbonate, organic base such as pyridine can be used in a solvent such as ethanol or N,N-dimethylformamide. The reaction can be implemented at a reaction temperature of −20° C. to 150° C., preferably 0° C. to refluxing temperature of solvent.

The hydrolysis reaction of the thirty-first process can be implemented under alkaline condition. For the alkaline condition, lithium hydroxide, sodium hydroxide, potassium hydroxide or the like is used. The reaction can be implemented at a reaction temperature of 0° C. to 80° C., preferably room temperature to 60° C.

The condensation reaction of the thirty-second process can be performed by leaving carboxyl group as it is or converting it to reactive derivatives.

As the “reactive derivative group of carboxyl group”, acid chloride, acid bromide, acid anhydride, carbonylimidazole or the like is mentioned. In the case of the reaction using reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The hydrolysis reaction of the thirty-third process can be performed under alkaline condition. For the alkaline condition, lithium hydroxide, sodium hydroxide, potassium hydroxide or the like is used. The reaction can be performed at a reaction temperature of 0° C. to 80° C., preferably room temperature to 60° C.

Moreover, optically active substances (1b') of the compounds of general formula (1b), the binding mode of A portion being —$CH_2CONH$—, in the compounds of said general formula (1) can be prepared, for example, through following processes (Scheme 7).

Scheme 7

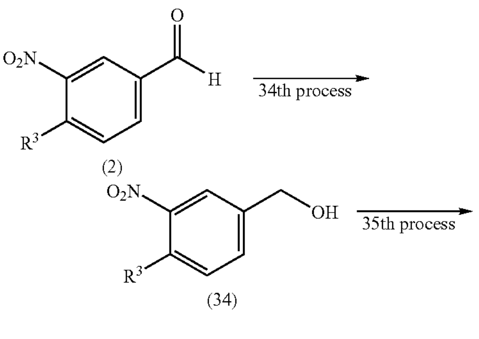

-continued

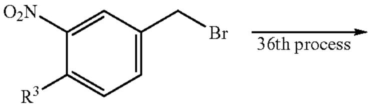

(35)

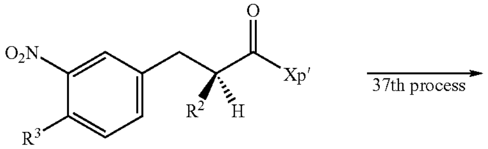

(36)

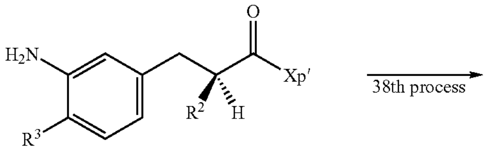

(37)

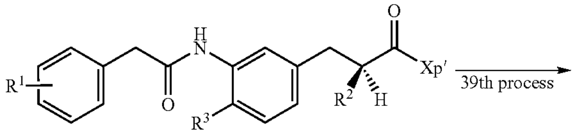

(38)

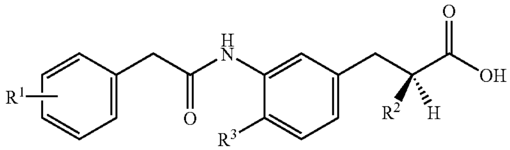

(1b')

Namely, optically active compounds represented by the general formula (1b')

(1b')

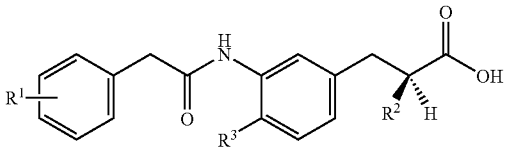

[wherein $R^1$ denotes a lower alkyl group with carbon atoms of 1 to 4, lower alkoxy group with carbon atoms of 1 to 3, tri-fluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a lower alkyl group with carbon atoms of 1 to 4 or lower alkoxy group with carbon atoms of 1 to 3, and $R^3$ denotes a lower alkoxy group with carbon atoms of 1 to 3], can be prepared by reducing (thirty-fourth process) compounds represented by the general formula (2)

(2)

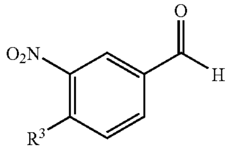

[wherein $R^3$ is as described above], to synthesize compounds represented by a general formula (34)

(34)

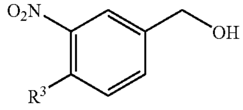

[wherein $R^3$ is as described above], by brominating (thirty-fifth process) these compounds to synthesize compounds represented by a general formula (35)

(35)

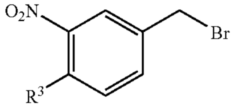

[wherein $R^3$ is as described above], by reacting (thirty-sixth process) these compounds with compounds represented by a general formula (39')

(39')

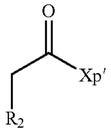

[wherein $R^2$ is as described above, and Xp' denotes chiral oxazolidinone, the absolute configuration being (R), such as (R)-4-benzyl-2-oxazolidinone-3-yl group, (R)-4-isopropyl-2-oxazolidinone-3-yl group or (R)-4-phenyl-2-oxazolidinone-3-yl group, chiral imidazolidinone, chiral cyclolactam, chiral sultam or the like], in the presence of base, to synthesize compounds represented by a general formula (36)

(36)

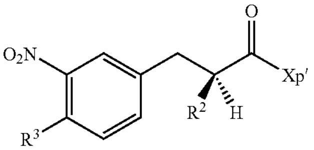

[wherein $R^2$, $R^3$ and Xp' are as described above], by reducing (thirty-seventh process) these compounds to synthesize compounds represented by a general formula (37)

(37)

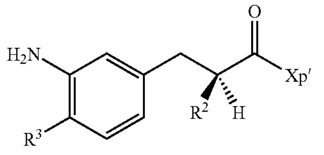

[wherein $R^2$, $R^3$ and Xp' are as described above], by reacting (thirty-eighth process) these compounds with compounds represented by the general formula (7)

(7)

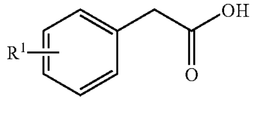

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents], to synthesize compounds represented by a general formula (38)

(38)

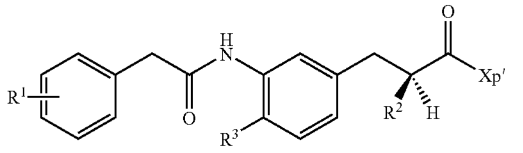

[wherein $R^1$, $R^2$, $R^3$ and Xp' are as described above], and by hydrolyzing (thirty-ninth process) COXp' portion of these compounds.

In the reaction of the thirty-fourth process, as a reducing agent, for example, diisobutylaluminum hydride, borane, alkylborane, sodium borohydride or the like can be used in a solvent such as tetrahydrofuran, diethyl ether or hexane. The reaction can be performed at a reaction temperature of −100° C. to 100° C., preferably −80° C. to room temperature.

The reaction of the thirty-fifth process can be implemented in a solvent such as methylene chloride, benzene or toluene, using brominating agent such as phosphorus tribromide, thionyl bromide, hydrobromic acid or triphenylphosphine and carbon tetrabromide. The reaction can be performed at a reaction temperature of −20° C. to 150° C., preferably 0° C. to −100° C.

In the reaction of the thirty-sixth process, as a base, for example, alkali metal hydride such as sodium hydride, organo-metallic compound such as butyl lithium or metal amide such as lithium diisopropylamide or sodium bis (trimethylsilyl)amide can be used in a solvent such as tetrahydrofuran, diethyl ether or hexane. The reaction can be performed at a reaction temperature of −100° C. to room temperature, preferably −80° C. to 0° C.

The reaction of the thirty-seventh process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably room temperature to 80° C.

The reaction of the thirty-eighth process can be performed by leaving carboxyl group as it is or converting it to reactive derivatives. As the "reactive derivative group of carboxyl group", acid chloride, acid bromide, acid anhydride, carbonylimidazole or the like is mentioned.

In the case of the reaction using reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxy-succinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The reaction of the thirty-ninth process can be performed under alkaline condition. For the alkaline condition, lithium hydroxide, sodium hydroxide, mixture of lithium hydroxide with hydrogen peroxide or the like is used. The reaction can be performed at a reaction temperature of −20° C. to 100° C., preferably 0° C. to 50° C.

Moreover, optically active substances (1c') of the compounds of general formula (1c), the binding mode of A portion being —$NHCOCH_2$—, in the compounds of said general formula (1) can be synthesized, for example, through following processes (Scheme 8).

Scheme 8

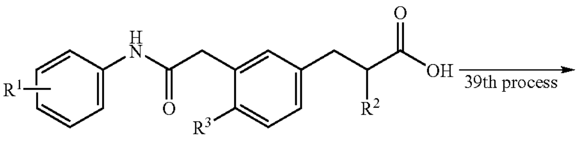

(1c)

-continued

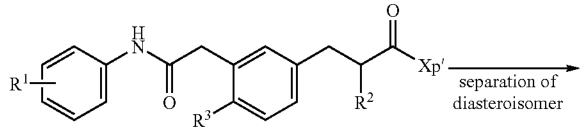

(39)

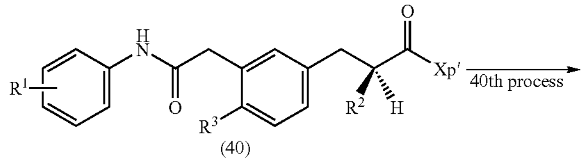

(40)

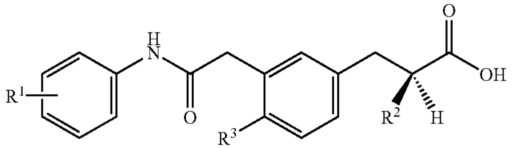

(1c')

Namely, optically active compounds represented by the general formula (1c')

(1c')

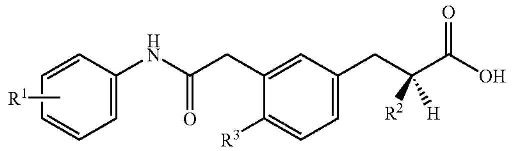

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a lower alkyl group with carbon atoms of 1 to 4 or lower alkoxy group with carbon atoms of 1 to 3, and $R^3$ denotes a lower alkoxy group with carbon atoms of 1 to 3], can be prepared by reacting compounds represented by the general formula (1c)

(1c)

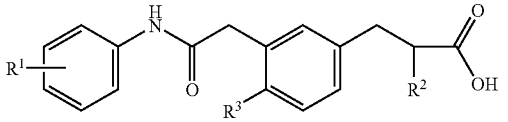

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a hydrogen atom, lower alkyl group with carbon atoms of 1 to 4 or lower alkoxy group with carbon atoms of 1 to 3, and $R^3$ denotes a lower alkoxy group with carbon atoms of 1 to 3], with pivaloyl chloride in the presence of base, to synthesize compounds represented by a general formula (41)

(41)

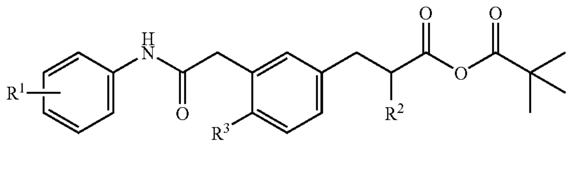

[wherein $R^1$, $R^2$ and $R^3$ are as described above], by reacting (thirty-ninth process) these compounds with compounds represented by a general formula (42)

(42)

Xp"—H

[wherein Xp" denotes an optically active chiral oxazolidinone derivative such as optically active 4-benzyl-2-oxazolidinone-3-yl group, 4-isopropyl-2-oxazolidinone-3-yl group or 4-phenyl-2-oxazolidinone-3-yl group, amide derivative, sultam derivative or the like], in the presence of base, to synthesize compounds represented by a general formula (39)

(39)

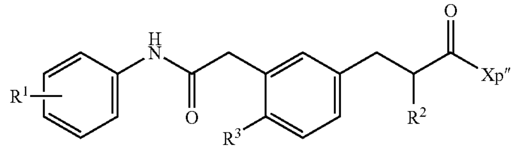

[wherein $R^1$, $R^2$, $R^3$ and Xp" are as described above], by recrystallizing or fractionating by means of column chromatography each diastereomer of these compounds, to obtain compounds represented by a general formula (40)

(40)

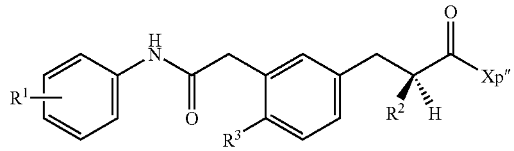

[wherein $R^1$, $R^2$, $R^3$ and Xp" are as described above], and by hydrolyzing (fortieth process) Xp" portion of these compounds.

In the reaction of the thirty-ninth process, first, the synthesis of the compounds represented by the general formula (41)

(41)

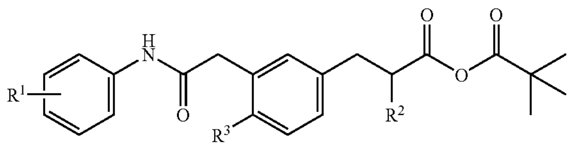

[wherein $R^1$, $R^2$ and $R^3$ are as described above], can be implemented in a solvent such as tetrahydrofuran, methylene chloride or diethyl ether, using tertiary amine such as triethylamine, diisopropylethylamine, ethyldimethylamine or pyridine. The reaction can be performed at a reaction temperature of −100° C. to room temperature, preferably −40° C. to 0° C.

Next, the reaction of compounds represented by the general formula (41)

(41)

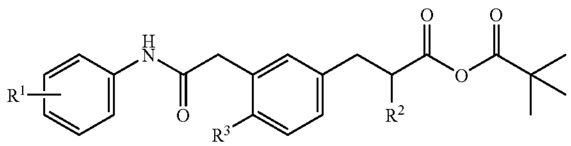

[wherein $R^1$, $R^2$ and $R^3$ are as described above], with general formula (42)

(42)

$$Xp''—H$$

[wherein Xp" is as described above], can be implemented in a solvent such as tetrahydrofuran, methylene chloride or diethyl ether, by reacting base of alkali metal hydride such as sodium hydride, organometallic compound such as butyl lithium, metal amide such as lithium diisopropylamide, metal alkoxide such as sodium methoxide or potassium t-butoxide. The reaction can be performed at a reaction temperature of −100° C. to room temperature, preferably −40° C. to 0° C.

The reaction of the fortieth process can be performed under alkaline condition. For the alkaline condition, lithium hydroxide, sodium hydroxide, mixture of lithium hydroxide with hydrogen peroxide or the like is used. The reaction can be performed at a reaction temperature of −20° C. to 100° C., preferably 0° C. to 50° C.

As the forms for administering the inventive novel compounds, solid compositions, liquid compositions and other compositions for oral administration, and injections, external medicines, suppositories, etc. for parenteral administration can be mentioned. The solid compositions for oral administration include tablets, pills, capsules, powders, granules, etc, The liquid compositions for oral administration include pharmaceutically acceptable emulsions, syrups, etc. The other compositions for oral administration include sprays. Moreover, the injections for parenteral administration include aseptic aqueous or nonaqueous solutions, suspensions, emulsions, etc.

Best Embodiment to Put the Invention into Practice

In following, the invention will be illustrated based on concrete examples, but the invention is not confined to these examples.

EXAMPLE 1

Ethyl 3-(3-amino-4-methoxyphenyl)-2-methoxypropanoate

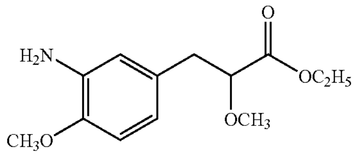

Under an argon atmosphere, stirring and cooling with ice, a solution of triethyl 2-phosphonobutyrate (5.00 g, 19.8 mmol) in anhydrous tetrahydrofuran (30 mL) was added dropwise slowly to a solution of sodium hydride (60% oil dispersion, 795 mg, 19.9 mmol) in anhydrous tetrahydrofuran (120 mL). After stirring for 1 hour at 0° C., a solution of 4-methoxy-3-nitrobenzaldehyde (3.26 g, 18.0 mmol) in anhydrous tetrahydrofuran (50 mL) was added dropwise, and the mixture was stirred for 1 hour at 0° C. and for 3 hours at room temperature. The reaction mixture was concentrated and ice water was added to the residue, which was extracted with ethyl acetate. The extracte was washed with water, brine and dried over anhydrous sodium sulfate, and then concentrated. The residue was purified by silica gel column chromatography (eluent n-hexane:ethyl acetate=8:1→2:1 v/v) to obtain 4.69 g (93%) of ethyl 2-ethyl-3-(4-methoxy-3-nitrophenyl)acrylate as colorless crystals.

Mass analysis m/z 281 ($M^+$).

Next, ethyl 2-ethyl-3-(4-methoxy-3-nitrophenyl)acrylate (4.50 g, 16.0 mmol), 10% palladium on carbon (1.50 g) and a 1:1 mixed solvent (150 mL) of tetrahydrofuran with ethanol were mixed and hydrogenation was carried out at an initial pressure of 294.3 kPa at room temperature. After completion of the reaction, the catalyst was removed by filtration and the filtrate was concentrated to afford 3.84 g (95%) of the title compound as colorless crystals.

Mass analysis m/z 253 ($M^+$).

EXAMPLES 2 AND 3

Similarly to Example 1, compounds shown in Table 1 were synthesized.

TABLE 1

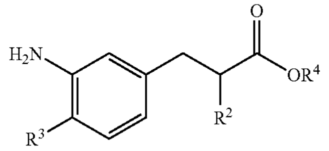

| Example | $R^2$ | $R^3$ | $R^4$ | Mass analysis (m/z) |
|---|---|---|---|---|
| 2 | $C_2H_5$ | $OCH_3$ | $C_2H_5$ | 251 ($M^+$) |
| 3 | $n-C_3H_7$ | $OCH_3$ | $C_2H_5$ | 265 ($M^+$) |

EXAMPLE 4

Methyl 3-(4-methoxy-3-nitrophenyl)propanoate

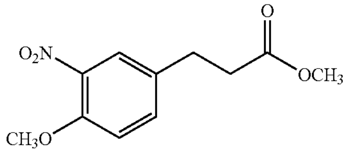

To 100 mL of concentrated nitric acid, cooled with ice, publicly known [e.g. Lebedev S. A. et al, J. Organo-met. Chem., 1988, 253] 4-methoxyphenylpropanoic acid (5.00 g, 25.7 mmol) was added little by little under stirring. After completion of the addition, the mixture was stirred further for 4 hours under cooling with ice. The reaction mixture was poured into ice water, which was extracted with methylene chloride. The extracte was dried over anhydrous sodium sulfate and concentrated. The residue was purified by silica gel column chromatography (eluent methylene chloride→methylene chloride:methanol=15:1 v/v) to obtain 2.70 g (44%), of the title compound as a faintly yellow oil.

$^{1}$H-NMR (400 MHz, $CDCl_3$) δ2.64 (2H, t, J=7.3 Hz), 2.95 (2H, t, J=7.3 Hz), 3.67 (3H, s), 3.94 (3H, s), 7.02 (1H, d, J=8.3 Hz), 7.39 (1H, dd, J=8.3, 2.4 Hz), 7.70 (1H, d, J=2.4 Hz).

EXAMPLE 5

Methyl 3-(3-amino-4-methoxyphenyl)propanoate

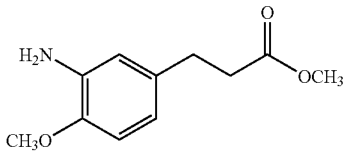

Methyl 4-methoxy-3-nitrophenylpropanoate (2.70 g, 11.3 mmol), 10% palladium on carbon (200 mg) and a mixed solvent (100 mL) of ethyl acetate with ethanol (1:1 v/v) were mixed and hydrogenation was carried at an initial pressure of 294.3 kPa. After completion of the hydrogenation, the catalyst was removed by filtration and the filtrate was concentrated to obtain 2.35 g (95%) of the title compound as a yellow oily product.

1H-NMR (400 MHz, $CDCl_3$) δ2.58 (2H, t, J=8.3 Hz), 2.82 (2H, t, J=8.3 Hz), 3.67 (3H, s), 3.82 (3H, s), 6.53–6.57 (2H, m), 6.70 (1H, d, J=8.3 Hz).

EXAMPLE 6

Ethyl 2-methoxy-3-[4-methoxy-3-[2-[4-(trifluoromethyl)phenyl]acetylamino]phenyl]propanoate

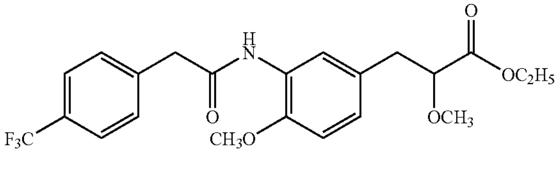

4-Trifluoromethylphenylacetic acid (316 mg, 1.50 mmol) and methyl 2-methoxy-3-(3-amino-4-methoxyphenyl)propanoate (253 mg, 0.999 mmol) were dissolved in dichloromethane (10 mL) and, after N-cyclohexyl-carbodiimido-N'-methyl polystyrene (1.46 g, 2.26 mmol) was added, the mixture was stirred for 30.5 hours at room temperature. The insolubles were removed by filtration and the filtrate was concentrated under reduced pressure to afford the title product quantitatively as brown crystals.

Mass analysis m/z 439 ($M^+$). $^{1}$H-NMR (400 MHz, $CDCl_3$) δ1.25 (3H, t, J=7.3 Hz), 2.91 (1H, dd, J=14.2, 7.8 Hz), 2.98 (1H, dd, J=14.2, 5.4 Hz), 3.33 (3H, s), 3.75 (3H, s), 3.80 (2H, s), 3.91–3.95 (1H, m), 4.19 (2H, q, J=7.3 Hz), 6.74 (1H, d, J=8.8 Hz), 6.90 (1H, dd, J=8.3, 2.0 Hz), 7.48 (2H, d, J=7.8 Hz), 7.65 (2H, d, J=8.3 Hz), 7.74 (1H, s), 8.25 (1H, d, J=2.0 Hz).

EXAMPLES 7 THROUGH 38

Similarly to Example 6, compounds in Table 2 were obtained.

TABLE 2

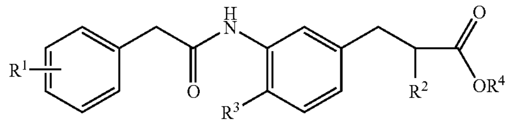

| Example | $R^1$ | $R^2$ | $R^3$ | $R^4$ | Mass analysis (m/z) |
|---|---|---|---|---|---|
| 7 | 4-$CF_3$ | H | $OCH_3$ | $CH_3$ | 395 ($M^+$) |
| 8 | 4-$OCH_2Ph$ | H | $OCH_3$ | $CH_3$ | 433 ($M^+$) |
| 9 | 4-OPh | H | $OCH_3$ | $CH_3$ | 419 ($M^+$) |
| 10 | 4-$OCH_3$ | H | $OCH_3$ | $CH_3$ | 357 ($M^+$) |
| 11 | 4-Ph | H | $OCH_3$ | $CH_3$ | 403 ($M^+$) |
| 12 | 4-$CF_3$ | $C_2H_5$ | $OCH_3$ | $C_2H_5$ | 437 ($M^+$) |
| 13 | 4-$OCH_2Ph$ | $C_2H_5$ | $OCH_3$ | $C_2H_5$ | 475 ($M^+$) |
| 14 | 4-OPh | $C_2H_5$ | $OCH_3$ | $C_2H_5$ | 461 ($M^+$) |
| 15 | 4-$OCH_3$ | $C_2H_5$ | $OCH_3$ | $C_2H_5$ | 399 ($M^+$) |
| 16 | 4-Ph | $C_2H_5$ | $OCH_3$ | $C_2H_5$ | 445 ($M^+$) |
| 17 | 4-$CH_3$ | $C_2H_5$ | $OCH_3$ | $C_2H_5$ | 383 ($M^+$) |
| 18 | 4-Cl | $C_2H_5$ | $OCH_3$ | $C_2H_5$ | 403 ($M^+$) |
| 19 | 4-F | $C_2H_5$ | $OCH_3$ | $C_2H_5$ | 387 ($M^+$) |
| 20 | 3-F | $C_2H_5$ | $OCH_3$ | $C_2H_5$ | 387 ($M^+$) |
| 21 | 2-F | $C_2H_5$ | $OCH_3$ | $C_2H_5$ | 387 ($M^+$) |
| 22 | 4-OPh(4-F) | $C_2H_5$ | $OCH_3$ | $C_2H_5$ | 479 ($M^+$) |
| 23 | 4-OPh(2-$OCH_3$) | $C_2H_5$ | $OCH_3$ | $C_2H_5$ | 491 ($M^+$) |
| 24 | 4-$CF_3$ | n-$C_3H_7$ | $OCH_3$ | $C_2H_5$ | 451 ($M^+$) |
| 25 | 4-$OCH_2Ph$ | n-$C_3H_7$ | $OCH_3$ | $C_2H_5$ | 489 ($M^+$) |
| 26 | 4-OPh | n-$C_3H_7$ | $OCH_3$ | $C_2H_5$ | 475 ($M^+$) |
| 27 | 4-$OCH_3$ | n-$C_3H_7$ | $OCH_3$ | $C_2H_5$ | 413 ($M^+$) |
| 28 | 4-Ph | n-$C_3H_7$ | $OCH_3$ | $C_2H_5$ | 459 ($M^+$) |
| 29 | 4-$CH_3$ | n-$C_3H_7$ | $OCH_3$ | $C_2H_5$ | 397 ($M^+$) |
| 30 | 4-Cl | n-$C_3H_7$ | $OCH_3$ | $C_2H_5$ | 417 ($M^+$) |
| 31 | 4-F | n-$C_3H_7$ | $OCH_3$ | $C_2H_5$ | 401 ($M^+$) |
| 32 | 3-F | n-$C_3H_7$ | $OCH_3$ | $C_2H_5$ | 401 ($M^+$) |
| 33 | 2-F | n-$C_3H_7$ | $OCH_3$ | $C_2H_5$ | 401 ($M^+$) |
| 34 | 4-OPh(4-F) | n-$C_3H_7$ | $OCH_3$ | $C_2H_5$ | 493 ($M^+$) |
| 35 | 4-OPh(2-$OCH_3$) | n-$C_3H_7$ | $OCH_3$ | $C_2H_5$ | 505 ($M^+$) |
| 36 | 4-$OCH_2Ph$ | $OCH_3$ | $OCH_3$ | $C_2H_5$ | 477 ($M^+$) |
| 37 | 4-OPh | $OCH_3$ | $OCH_3$ | $C_2H_5$ | 463 ($M^+$) |
| 38 | 4-Ph | $OCH_3$ | $OCH_3$ | $C_2H_5$ | 447 ($M^+$) |

EXAMPLE 39

2-Methoxy-3-[4-methoxy-3-[2-[4-(trifluoromethyl)phenyl]acetylamino]phenyl]propanoic acid

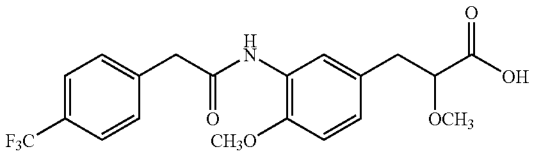

Ethyl 2-methoxy-3-[4-methoxy-3-[2-[4-(trifluoromethyl)phenyl]acetylamino]phenyl]propanoate (442 mg, 0.986 mmol), methanol (9 mL) and 1 mol/L aqueous solution of sodium hydroxide (5 mL) were mixed. After stirring for 5 hours at room temperature, the reaction mixture was concentrated under reduced pressure. The residue was dissolved in water, washed with ether, and then made acidic with diluted hydrochloric acid. The precipitates produced were filtered and dried to afford 379 mg (93%) of the title compound as pale yellow crystals.

Melting point 124–125° C. Mass analysis m/z 411 ($M^+$). Elemental analysis $C_{20}H_{20}F_3NO_5$: Calcd. (%) C, 58.39; H, 4.90; N, 3.40. Found (%) C, 58.39; H, 4.83; N, 3.52.

EXAMPLES 40 THROUGH 71

Similarly to Example 39, compounds in Table 3 were obtained.

TABLE 3

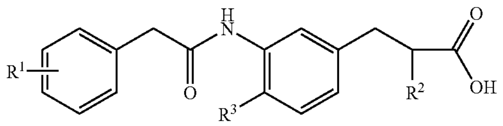

| Example | $R^1$ | $R^2$ | $R^3$ | Melting point(° C.) | Charac. formula | Elemental analysis(%) |
|---|---|---|---|---|---|---|
| 40 | 4-$CF_3$ | H | $OCH_3$ | 186–187 | $C_{19}H_{18}F_3NO_4$ | Calc.; C 59.84, H 4.76, N 3.67<br>Found; C 59.73, H 4.77, N 3.67 |
| 41 | 4-$OCH_3$ | H | $OCH_3$ | 160–161 | $C_{19}H_{21}NO_5$ | Calc. ; C 66.46, H 6.16, N 4.08<br>Found; C 66.39, H 6.07, N 4.05 |
| 42 | 4-$OCH_2Ph$ | H | $OCH_3$ | 151–152 | $C_{25}H_{25}NO_5$ | Calc.; C 71.58, H 6.01, N 3.34<br>Found; C 71.29, H 5.99, N 3.44 |
| 43 | 4-OPh | H | $OCH_3$ | 146–147 | $C_{24}H_{23}NO_5$ | Calc.; C 71.10, H 5.72, N 3.45<br>Found; C 71.13, H 5.71, N 3.54 |
| 44 | 4-Ph | H | $OCH_3$ | 177 | $C_{24}H_{23}NO_4$ | Calc. ; C 74.02, H 5.95, N 3.60<br>Found; C 73.80, H 5.97, N 3.60 |
| 45 | 4-$CF_3$ | $C_2H_5$ | $OCH_3$ | (amorphous) | $C_{21}H_{22}F_3NO_4$ | Calc.; C 61.61, H 5.42, N 3.42<br>Found; C 61.43, H 5.44, N 3.45 |
| 46 | 4-$OCH_2Ph$ | $C_2H_5$ | $OCH_3$ | (amorphous) | $C_{27}H_{29}NO_5$ | Calc.; C 72.46, H 6.53, N 3.13<br>Found; C 72.41, H 6.56, N 3.06 |
| 47 | 4-OPh | $C_2H_5$ | $OCH_3$ | (amorphous) | $C_{26}H_{27}NO_5 \cdot$ 1/10$H_2O$ | Calc.; C 71.74, H 6.30 ,N 3.22<br>Found; C 71.64, H 6.39, N 3.24 |
| 48 | 4-$OCH_3$ | $C_2H_5$ | $OCH_3$ | 135–136 | $C_{21}H_{25}NO_5$ | Calc.; C 67.91, H 6.78, N 3.77<br>Found; C 67.85, H 6.81, N 3.81 |
| 49 | 4-Ph | $C_2H_5$ | $OCH_3$ | 142–143 | $C_{26}H_{27}NO_4$ | Calc.; C 74.80, H 6.52, N 3.35<br>Found; C 74.75, H 6.64, N 3.38 |
| 50 | 4-CH3 | $C_2H_5$ | $OCH_3$ | 134–135 | $C_{21}H_{25}NO_4$ | Calc.; C 70.96, H 7.09, N 3.94<br>Found; C 70.86, H 7.10, N 4.02 |
| 51 | 4-Cl | $C_2H_5$ | $OCH_3$ | 112–113 | $C_{20}H_{22}ClNO_4$ | Calc.; C 63.91, H 5.90, N 3.73<br>Found; C 63.76, H 5.88, N 3.77 |
| 52 | 4-F | $C_2H_5$ | $OCH_3$ | 97–98 | $C_{20}H_{22}FNO_4$ | Calc.; C 66.84, H 6.17, N 3.90<br>Found; C 66.68, H 6.13, N 3.93 |
| 53 | 3-F | $C_2H_5$ | $OCH_3$ | (amorphous) | $C_{20}H_{22}FNO_4$ | Calc.; C 66.84, H 6.17, N 3.90<br>Found; C 66.68, H 6.20, N 3.83 |
| 54 | 2-F | $C_2H_5$ | $OCH_3$ | 89 | $C_{20}H_{22}FNO_4$ | Calc.; C 66.84, H 6.17, N 3.90<br>Found; C 66.85, H 6.17, N 4.01 |
| 55 | 4-OPh(4-F) | $C_2H_5$ | $OCH_3$ | 101–102 | $C_{26}H_{26}FNO_5 \cdot$ 3/10$H_2O$ | Calc.; C 68.35, H 5.87, N 3.07<br>Found; C 68.26, H 5.81, N 3.17 |
| 56 | 4-OPh-<br>(2-$OCH_3$) | $C_2H_5$ | $OCH_3$ | (amorphous) | $C_{27}H_{29}NO_6$ | Calc.; C 69.96, H 6.31, N 3.02<br>Found; C 69.68, H 6.35, N 3.11 |
| 57 | 4-$CF_3$ | n-$C_3H_7$ | $OCH_3$ | (amorphous) | $C_{22}H_{24}F_3NO_4 \cdot$ 2/5$H_2O$ | Calc.; C 61.36, H 5.80, N 3.25<br>Found; C 61.27, H 5.50, N 3.01 |
| 58 | 4-$OCH_2Ph$ | n-$C_3H_7$ | $OCH_3$ | 108–110 | $C_{28}H_{31}NO_5$ | Calc.; C 72.86, H 6.77, N 3.03<br>Found C 72.79 , H 6.82, N 3.08 |
| 59 | 4-OPh | n-$C_3H_7$ | $OCH_3$ | 116 | $C_{27}H_{29}NO_5$ | Calc.; C 72.46, H 6.53, N 3.13<br>Found; C 72.43, H 6.54, N 3.24 |
| 60 | 4-$OCH_3$ | n-$C_3H_7$ | $OCH_3$ | 132–133 | $C_{22}H_{27}NO_5$ | Calc.; C 68.55, H 7.06, N 3.63<br>Found; C 68.32, H 7.04, N 3.70 |
| 61 | 4-Ph | n-$C_3H_7$ | $OCH_3$ | 145–146 | $C_{27}H_{29}NO_4$ | Calc.; C 75.15, H 6.77, N 3.25<br>Found; C 75.02, H 6.87, N 3.26 |
| 62 | 4-$CH_3$ | n-$C_3H_7$ | $OCH_3$ | 115–116 | $C_{22}H_{27}NO_4$ | Calc.; C 71.52, H 7.37, N 3.79<br>Found; C 71.31, H 7.35, N 3.80 |

TABLE 3-continued

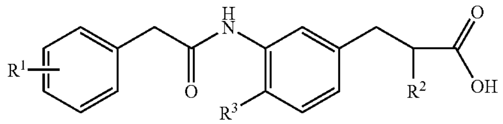

| Example | $R^1$ | $R^2$ | $R^3$ | Melting point(° C.) | Charac. formula | Elemental analysis(%) |
|---|---|---|---|---|---|---|
| 63 | 4-Cl | n-$C_3H_7$ | $OCH_3$ | 110–111 | $C_{21}H_{24}ClNO_4$ | Calc.; C 64.69, H 6.20, N 3.59<br>Found; C 64.62, H 6.13, N 3.61 |
| 64 | 4-F | n-$C_3H_7$ | $OCH_3$ | 105–106 | $C_{21}H_{24}FNO_4$ | Calc.; C 67.54, H 6.48, N 3.75<br>Found; C 67.46, H 6.43, N 3.84 |
| 65 | 3-F | n-$C_3H_7$ | $OCH_3$ | (amorphous) | $C_{21}H_{24}FNO_4 \cdot 1/5H_2O$ | Calc.; C 66.90, H 6.52, N 3.72<br>Found; C 66.98, H 6.50, N 3.80 |
| 66 | 2-F | n-$C_3H_7$ | $OCH_3$ | 112–113 | $C_{21}H_{24}FNO_4$ | Calc.; C 67.54, H 6.48, N 3.75<br>Found; C 67.46, H 6.40, N 3.78 |
| 67 | 4-OPh-(4-F) | n-$C_3H_7$ | $OCH_3$ | 123–124 | $C_{27}H_{28}FNO_5 \cdot 2/5H_2O$ | Calc.; C 68.60, H 6.14, N 2.96<br>Found; C 68.30, H 6.04, N 3.08 |
| 68 | 4-OPh-(2-$OCH_3$) | n-$C_3H_7$ | $OCH_3$ | (amorphous) | $C_{28}H_{31}NO_6 \cdot 1/10H_2O$ | Calc.; C 70.16, H 6.56, N 2.92<br>Found; C 70.16, H 6.57, N 2.93 |
| 69 | 4-$OCH_2$Ph | $OCH_3$ | $OCH_3$ | (amorphous) | $C_{26}H_{27}NO_6 \cdot 1/5H_2O$ | Calc.; C 68.92, H 6.10, N 3.09<br>Found; C 69.03, H 6.30, N 3.12 |
| 70 | 4-OPh | $OCH_3$ | $OCH_3$ | (amorphous) | $C_{25}H_{25}NO_6$ | Calc.; C 68.95, H 5.79, N 3.22<br>Found; C 68.86, H 5.96, N 3.19 |
| 71 | 4-Ph | $OCH_3$ | $OCH_3$ | 112–114 | $C_{25}H_{25}NO_5$ | Calc.; C 71.58, H 6.01, N 3.34<br>Found; C 71.48, H 6.09, N 3.35 |

EXAMPLE 72

Ethyl 2-methylthio-2-(5-formyl-2-methoxyphenyl)acetate

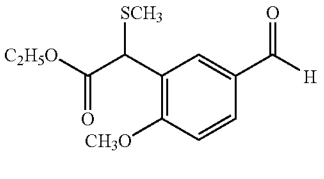

To a solution of 4-methoxybenzaldehyde (7.46 g, 57.3 mmol) in methylene chloride (250 mL), a solution of anhydrous tin chloride (IV) (6.49 mL, 54.7 mmol) in methylene chloride (100 mL) was added dropwise slowly under an argon atmosphere, stirring and cooling with ice. After stirring for 15 minutes at room temperature, a solution of ethyl 2-chloro-2-methylthioacetate (9.24 g, 54.8 mmol) in a mixed solution (50 mL) of methylene chloride with carbon tetrachloride (1:1) was added dropwise. After refluxing for 24 hours, the reaction mixture was allowed to stand for cooling. This was poured in ice water and the organic layer was separated. Then, the aqueous layer was extracted with methylene chloride. Respective organic layers were combined, washed with water, saturated aqueous solution of sodium hydrogencarbonate and brine, then dried over anhydrous sodium sulfate, and concentrated. The residue was purified by silica gel column chromatography (eluent n-hexane:ethyl acetate=5:1 v/v) to afford 7.59 g (52%) of the title compound as a yellow oil.

Mass analysis m/z 268 ($M^+$).

EXAMPLE 73

Benzyl 2-methylthio-2-(5-formyl-2-methoxyphenyl)acetate

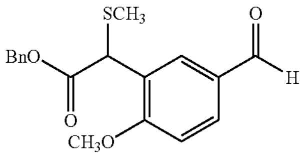

Ethyl 2-methylthio-2-(5-formyl-2-methoxyphenyl)acetate (4.80 g, 17.9 mmol), ethanol (30 mL) and 10% aqueous solution of sodium hydroxide (20 mL) were mixed and the mixture was stirred for 3 hours at room temperature. The reaction mixture was poured in ice water and made acidic with concentrated hydrochloric acid, which was then extracted with ethyl acetate. The extracte was washed with water, dried over anhydrous sodium sulfate, and then concentrated to afford 4.00 g of crude 2-methylthio-2-(5-formyl-2-methoxyphenyl)acetic acid as yellow crystals (this compound was used for next reaction without further purification). Next, 2-methylthio-2-(5-formyl-2-methoxyphenyl)acetic acid (4.00 g, 16.4 mmol) and N,N-dimethylformamide (50 mL) were mixed and, after anhydrous potassium carbonate (3.71 g, 26.8 mmol) and benzyl bromide (3.06 g, 17.9 mmol) were added at room temperature under stirring, the mixture was stirred for 5 hours. The reaction mixture was poured in ice water and extracted with ether. The extracted solution was washed with water and brine, and then dried over anhydrous sodium sulfate. The reaction mixture was concentrated and the residue was purified by silica gel column chromatography (eluate n-hexane:ethyl acetate=6:1 v/v) to afford 4.50 g (76%) of the title compound as a light brown oil.

Mass analysis m/z 330 ($M^+$).

EXAMPLE 74

Benzyl 2-methylthio-2-[5-[1-(2-ethoxycarbonyl)phenyl]-2-methoxyphenyl]acetate

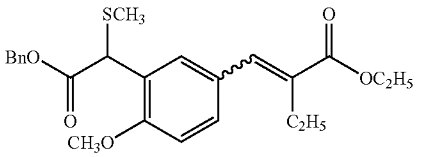

Under an argon atmosphere, triethyl 2-phosphonobutyrate (3.77 g, 14.9 mmol) was dissolved in dehydrated tetrahydrofuran (40 mL) and potassium tert-butoxide (1.68 g, 15.0 mmol) was added under stirring and cooling with ice. After completion of the addition, the mixture was stirred for 1 hour. Following this, benzyl 2-methylthio-2-(5-formyl-2-methoxyphenyl)acetate (4.49 g, 13.6 mmol) dissolved in dehydrated tetrahydrofuran (30 mL) was added and the mixture was stirred for 6 hours at room temperature. The reaction mixture was concentrated and ice water was added, which was made acidic with 1 mol/L hydrochloric acid. The reaction mixture was extracted with ethyl acetate. The extracte was washed with water and brine, dried over anhydrous sodium sulfate, and then concentrated. The residue was purified by silica gel column chromatography (eluent n-hexane:ethyl acetate=9:1 v/v) to afford 4.55 g (78%) of the title compound as a colorless oil.

Mass analysis m/z 428 ($M^+$).

EXAMPLE 75

Benzyl 2-[5-[1-(2-ethoxycarbonyl)butenyl]-2-methoxyphenyl]acetate

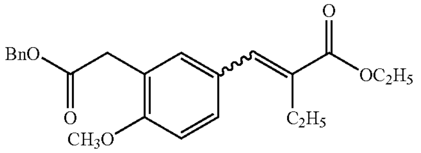

Benzyl 2-methylthio-2-[5-[1-(2-ethoxycarbonyl)butenyl]-2-methoxyphenyl]acetate (2.14 g, 4.99 mmol) and glacial acetic acid (100 mL) were mixed and zinc powder (13.0 g, 199 mmol) was added under stirring at room temperature. After stirring for 6 hours at room temperature, the insolubles were remove by filtration and the filtrate was concentrated. The residue was dissolved into ethyl acetate (50 mL), washed with water and brine, then dried over anhydrous sodium sulfate and concentrated to afford 1.86 g (97%) of the title compound as a pale yellow oil.

Mass analysis m/z 382 ($M^+$).

EXAMPLE 76

2-[5-(2-ethoxycarbonyl)butyl-2-methoxyphenyl]-acetic acid

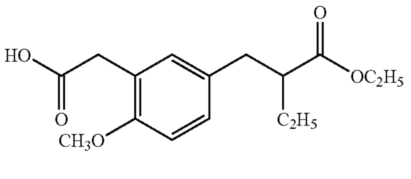

Benzyl 2-[5-[1-(2-ethoxycarbonyl)butenyl]-2-methoxyphenyl]acetate (1.85 g, 4.84 mmol), 5% palladium on carbon (400 mg), tetrahydrofuran (50 mL) and ethanol (50 mL) were mixed and hydrogenation was carried out for 8 hours at room temperature. The catalyst was removed by filtration and the filtrate was concentrated to afford 1.42 g (100%) of the title compound as a yellow oily product.

Mass analysis m/z 294 ($M^+$).

EXAMPLE 77

Ethyl 2-ethyl-3-[4-methoxy-3-[[N-[4-(trifluoromethyl)phenyl]carbamoyl]methyl]phenyl]propionate

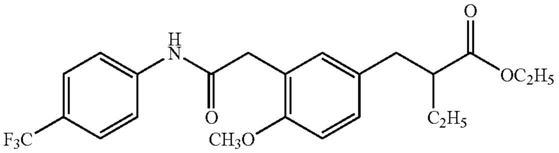

2-[5-(2-Ethoxycarbonyl)butyl-2-methoxyphenyl]acetic acid (500 mg, 1.70 mmol), 4-trifluoromethylaniline (300 mg, 1.86 mmol), triethylamine (260 μL, 1.87 mmol) and dehydrated N,N-dimethylformamide (6 mL) were mixed and, under an argon atmosphere, stirring and cooling with ice, diethyl cyanophosphate (283 μL, 1.87 mmol) was added. After stirring for 6 hours at room temperature, the mixture was allowed to stand overnight. Ice water was added to the reaction mixture, which was then extracted with ethyl acetate. The extracte was washed with water and brine, dried over anhydrous sodium sulfate and concentrated. The residue was purified by silica gel column chromatography (eluent n-hexane:ethyl acetate=6:1 v/v) to afford 210 mg (28%) of the title compound as a yellow oil.

Mass analysis m/z 437 ($M^+$).

EXAMPLES 78 THROUGH 87

Similarly to Examples 77, compounds in Table 4 were obtained.

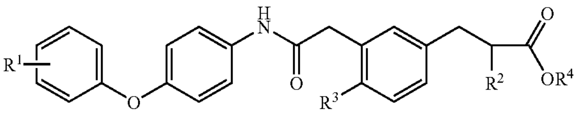

| Example | $R^1$ | $R^2$ | $R^3$ | $R^4$ | Mass analysis (m/z) |
|---|---|---|---|---|---|
| 78 | 2-$CH_3$ | $C_2H_5$ | $OCH_3$ | $C_2H_5$ | 475 ($M^+$) |
| 79 | 3-$CH_3$ | $C_2H_5$ | $OCH_3$ | $C_2H_5$ | 475 ($M^+$) |
| 80 | 4-$CH_3$ | $C_2H_5$ | $OCH_3$ | $C_2H_5$ | 475 ($M^+$) |
| 81 | 2-$OCH_3$ | $C_2H_5$ | $OCH_3$ | $C_2H_5$ | 491 ($M^+$) |
| 82 | 3-$OCH_3$ | $C_2H_5$ | $OCH_3$ | $C_2H_5$ | 491 ($M^+$) |

-continued

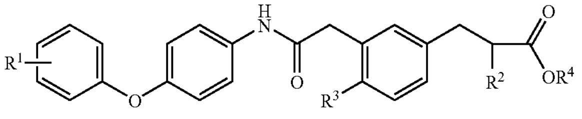

| Example | $R^1$ | $R^2$ | $R^3$ | $R^4$ | Mass analysis (m/z) |
|---|---|---|---|---|---|
| 83 | 4-$OCH_3$ | $C_2H_5$ | $OCH_3$ | $C_2H_5$ | 491 ($M^+$) |
| 84 | 2-F | $C_2H_5$ | $OCH_3$ | $C_2H_5$ | 479 ($M^+$) |
| 85 | 3-F | $C_2H_5$ | $OCH_3$ | $C_2H_5$ | 479 ($M^+$) |
| 86 | 4-F | $C_2H_5$ | $OCH_3$ | $C_2H_5$ | 479 ($M^+$) |
| 87 | 4-Cl | $C_2H_5$ | $OCH_3$ | $C_2H_5$ | 495 ($M^+$) |

EXAMPLE 88

2-Ethyl-3-[4-methoxy-3-[[N-[4-(trifluoromethyl) phenyl]carbamoyl]methyl]phenyl]propanoic acid

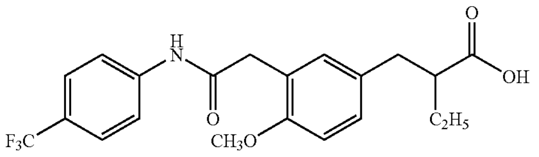

Ethyl 2-ethyl-3-[4-methoxy-3-[[N-[4-(trifluoromethyl) phenyl]carbamoyl]methyl]phenyl]propanoate (206 mg, 0.471 mmol), ethanol (5 mL) and 10% aqueous solution of sodium hydroxide (3 mL) were mixed and the mixture was stirred for 6 hours at room temperature. The reaction mixture was poured into ice water and made acidic with 1 mol/L hydrochloric acid, which was then extracted with ethyl acetate. The extracte was washed with water and brine, dried over anhydrous sodium sulfate, and then concentrated. The residue was purified by silica gel column chromatography (eluent n-hexane:ethyl acetate=4:1→1:1 v/v) and recrystallized from a mixed solvent of n-hexane with ethyl acetate to afford 142 mg (73%) of the title compound as colorless powder.

Melting point 136–137° C.

Mass analysis m/z 409 ($M^+$). Elemental analysis C21H22F3NO4 (409.40): Calc. C, 61.61; H, 5.42; N, 3.42. Found C, 61.48; H, 5.39; N, 3.51. $^1$H-NMR (400 MHz, CDCl3) δ0.96 (3H, t, J=7.3 Hz), 1.54–1.73 (2H, m), 2.55–2.62 (1H, m), 2.74 (1H, dd, J=14.2, 5.9 Hz), 2.88 (1H, dd, J=14.2, 8.8 Hz), 3.68 (2H, s), 3.91 (3H, s), 6.87 (1H, d, J=9.3 Hz), 7.11–7.14 (2H, m), 7.51 (2H, d, J=8.8 Hz), 7.54 (2H, d, J=8.8 Hz), 7.90 (1H, s).

EXAMPLES 89 THROUGH 98

Similarly to Example 88, compounds in Table 5 were obtained.

TABLE 5

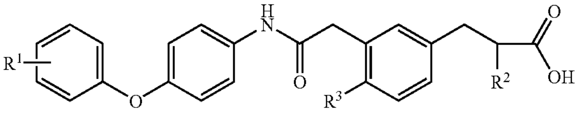

| Example | $R^1$ | $R^2$ | $R^3$ | Melting point(° C.) | Mass analysis(m/z) |
|---|---|---|---|---|---|
| 89 | 2-$CH_3$ | $C_2H_5$ | $OCH_3$ | 130–132 | 447 ($M^+$) |
| 90 | 3-$CH_3$ | $C_2H_5$ | $OCH_3$ | 123–125 | 447 ($M^+$) |
| 91 | 4-$CH_3$ | $C_2H_5$ | $OCH_3$ | 147–149 | 447 ($M^+$) |
| 92 | 2-$OCH_3$ | $C_2H_5$ | $OCH_3$ | 100–102 | 463 ($M^+$) |
| 93 | 3-$OCH_3$ | $C_2H_5$ | $OCH_3$ | 120–122 | 463 ($M^+$) |
| 94 | 4-$OCH_3$ | $C_2H_5$ | $OCH_3$ | 127–129 | 463 ($M^+$) |
| 95 | 2-F | $C_2H_5$ | $OCH_3$ | 136–137 | 451 ($M^+$) |
| 96 | 3-F | $C_2H_5$ | $OCH_3$ | 111–113 | 451 ($M^+$) |
| 97 | 4-F | $C_2H_5$ | $OCH_3$ | 85–87 | 451 ($M^+$) |
| 98 | 4-Cl | $C_2H_5$ | $OCH_3$ | 94–96 | 467 ($M^+$) |

EXAMPLE 99

Ethyl 2-ethyl-3-(4-methoxyphenyl)acrylate

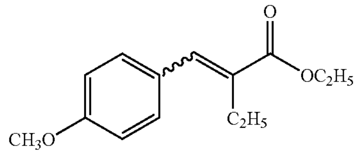

Under an argon atmosphere, stirring and cooling with ice, a solution of triethyl 2-phosphonobutyrate (5.55 g, 22.0 mmol) in anhydrous tetrahydrofuran (5 mL) was added dropwise to a solution of potassium tert-butoxide (2.47 g, 22.0 mmol) in anhydrous tetrahydrofuran (30 mL), and then the mixture was stirred for 20 minutes. Next, after a solution of p-anisadehyde (2.72 g, 20.0 mmol) in anhydrous tetrahydrofuran (5 mL) was added, the mixture was stirred for 1 hour under cooling with ice and for 4 hours at room temperature. Cooled 0.5 mol/L hydrochloric acid (100 mL) was added to the reaction mixture, which was extracted with ethyl acetate. The organic layer was washed with water and brine, then dried over anhydrous sodium sulfate and concentrated. The residue was purified by silica gel column chromatography (eluent n-hexane:ethyl acetate=15:1 v/v) to afford 4.58 g (98%) of the title compound as a colorless oily product.

Mass analysis m/z 234 ($M^+$).

EXAMPLE 100

Ethyl 2-ethyl-3-(4-methoxyphenyl)propanoate

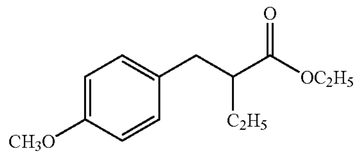

Ethyl 2-ethyl-3-(4-methoxyphenyl)acrylate (4.58 g, 19.5 mmol), 5% palladium on carbon (500 mg) and ethyl acetate (100 mL) were mixed and hydrogenated for 8 hours at room temperature. After the catalyst was removed by filtration, the filtrate was concentrated to afford 4.63 g (100%) of the title compound as a pale yellow oil.

Mass analysis m/z 236 ($M^+$).

EXAMPLE 101

Ethyl 3-(3-acetyl-4-methoxyphenyl)-2-ethylpropanoate

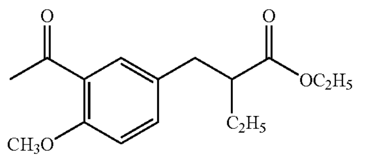

Under stirring and cooling with ice, acetyl chloride (1.00 mL, 14.1 mmol) wad added dropwise to a suspension of aluminum chloride (III) (1.78 g, 13.3 mmol) in dichloromethane (30 mL), and then the mixture was stirred for 30 minutes. Next, a solution of ethyl 2-ethyl-3-(4-methoxyphenyl)propanoate (2.10 g, 8.89 mmol) in dichloromethane (10 mL) was added dropwise. After stirring for 1 hour under cooling with ice, the mixture was allowed to stand overnight at room temperature. The reaction mixture was poured in ice water, the dichloro-methane layer was separated. and the aqueous layer was extracted with dichloromethane. The organic layers were combined and washed with water and brine, dried over anhydrous sodium sulfate, and then concentrated. The residue was purified by silica gel column chromatography (eluent n-hexane:ethyl acetate=6:1 v/v) to afford 1.21 g (49%) of the title compound as a yellow oily product.

Mass analysis m/z 278 ($M^+$).

EXAMPLE 102

Ethyl 3-[3-(2-ethoxycarbonylacetyl)-4-methoxyphenyl]-2-ethylpropanoate

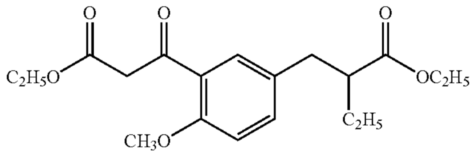

To anhydrous diethyl ether (20 mL), sodium hydride (60% oil dispersion, 1.27 g, 52.9 mmol) was added under stirring and cooling with ice. Successively, after diethyl carbonate (2.25 g, 19.0 mmol) was added, the mixture was stirred for 30 minutes at room temperature. Following this, a mixture of ethyl 3-(3-acetyl-4-methoxyphenyl)-2-ethylpropanoate (3.53 g, 12.7 mmol), anhydrous diethyl ether (10 mL) and absolute ethanol (0.24 mL) was added dropwise over 20 minutes, and then the mixture was refluxed for 6 hours. After cooling, the reaction mixture was added slowly to a mixed solution of 2 mol/L hydrochloric acid (45 mL) with ethyl acetate (80 mL) under stirring and cooling with ice. The organic layer was separated, and the aqueous layer was extracted with ethyl acetate. The organic layers were combined and washed with water and brine, dried over anhydrous sodium sulfate, and then concentrated. The residue was purified by silica gel column chromatography (eluent n-hexane:ethyl acetate=9:1 v/v) to afford 2.59 g (58%) of the title compound as a pale yellow oil.

Mass analysis m/z 350 ($M^+$).

EXAMPLE 103

Ethyl 3-[3-[2-ethoxycarbonyl-3-[4-(trifluoromethyl)phenyl]propionyl]-4-methoxyphenyl]-2-ethylpropanoate

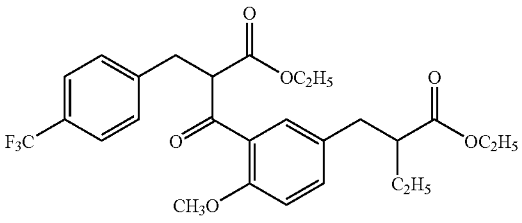

Under an argon atmosphere, stirring and cooling with ice, sodium hydride (60% oil dispersion, 296 mg, 7.40 mmol) was added little by little to a solution of ethyl 3-[3-(2-ethoxycarbonylacetyl)-4-methoxyphenyl]-2-ethylpropanoate (2.59 g, 7.39 mmol) in anhydrous tetrahydrofuran (30 mL), and then the mixture was stirred for 20 minutes under cooling with ice and for 30 minutes at room temperature. Following this, a solution of 4-(trifluoromethyl)benzylbromide (1.77 g, 7.40 mmol) in anhydrous tetrahydrofuran (10 mL) was added dropwise. After completion of the dropwise addition, the mixture was refluxed for 6 hours. After cooling, a mixture of 1 mol/L hydrochloric acid (15 mL) with ice water (100 mL) was added thereto, which was extracted with ethyl acetate. The organic layer was washed with water and brine, dried over anhydrous sodium sulfate, and then concentrated. The residue was purified by silica gel column chromatography (eluent n-hexane:ethyl acetate=8:1 v/v) to afford 3.70 g (98%) of the title compound as a pale yellow oil.

Mass analysis m/z 508 ($M^+$).

EXAMPLE 104

2-Ethyl-3-[3-[3-[4-(trifluoromethyl)phenyl]propionyl]-4-methoxyphenyl]propanoic acid

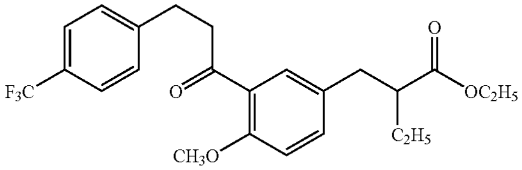

A mixture of ethyl-3-[3-[2-ethoxycarbonyl-3-[4-(trifluoromethyl)phenyl]propionyl]-4-methoxyphenyl]-2-ethylpropanoate (2.62 g, 5.15 mmol), glacial acetic acid (10 mL) and concentrated hydrochloric acid (5 mL) was refluxed for 5 hours. After cooling, the mixture was poured into ice water, which was extracted with ethyl acetate. The organic layer was washed with water and brine, dried over anhydrous sodium sulfate, and then concentrated. The residue was purified by silica gel column chromatography (eluent n-hexane:ethyl acetate:acetic acid=400:100:1.5 v/v/v) to afford 1.47 g (70%) of the title compound as a pale yellow oil.

Mass analysis m/z 408 ($M^+$). Elemental analysis C22H23F3O4 (408.41): Calc. (%) C, 64.70; H, 5.68. Found (%) C, 64.42; H, 5.71. $^1$H-NMR (400 MHz, CDCl3) δ0.95 (3H, t, J=7.3 Hz), 1.54–1.69 (2H, m), 2.54–2.61 (1H, m), 2.73 (1H, dd, J=13.7, 6.8 Hz), 2.92 (1H, dd, J=13.7, 7.8 Hz), 3.06 (2H, t, J=7.3 Hz), 3.31 (2H, t, J=7.3 Hz), 3.85 (3H, s), 6.87 (1H, d, J=8.8 Hz), 7.28 (1H, dd, J=8.3, 2.4 Hz), 7.34 (2H, d, J=7.8 Hz), 7.52–7.54 (3H, m).

EXAMPLE 105

2-Ethyl-3-[3-[3-[4-(trifluoromethyl)phenyl]propyl]-4-methoxyphenyl]propanoic acid

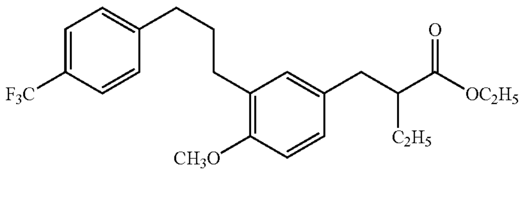

A solution of 2-ethyl-3-[3-[3-[4-(trifluoromethyl)phenyl]propionyl]-4-methoxyphenyl]propanoic acid (224 mg, 0.548 mmol) in ethanol (30 mL) was hydrogenated for 7 hours with 10% palladium on carbon (250 mg) at room temperature under a hydrogen pressure of 392 kPa. The catalyst was removed by filtration and the filtrate was concentrated. The residue was purified by means of thin layer silica gel column chromatography (eluent: n-hexane:ethyl acetate:acetic acid=200:100:2 v/v/v) to afford 185 mg (86%) of the title compound as a yellow oil.

Mass analysis m/z 394 ($M^+$). Elemental analysis C22H25F3O3 (394.43): Calc. (%) C, 66.99; H, 6.39. Found (%) C, 66.92; H, 6.39. $^1$H-NMR (400 MHz, CDCl3) δ0.94 (3H, t, J=7.3 Hz), 1.52–1.67 (2H, m), 1.87–1.94 (2H, m), 2.53–2.71 (6H, m), 2.88 (1H, dd, J=7.8, 13.7 Hz), 3.78 (3H, s), 6.74 (1H, d, J=8.3 Hz), 6.92 (1H, d, J=2.4 Hz), 6.98 (1H, dd, J=8.3, 2.4 Hz), 7.29 (2H, d, J=8.3 Hz), 7.52 (2H, d, J=8.3 Hz).

EXAMPLE 106

Ethyl 2-ethyl-3-(3-formyl-4-methoxyphenyl)propanoate

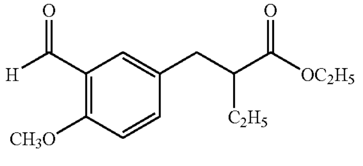

Under an argon atmosphere, stirring and cooling at −20° C., titanium chloride (IV) (35.0 mL, 318 mmol) and dichloromethyl methyl ether (13.4 mL, 148 mmol) were added dropwise in sequence to a solution of ethyl 2-ethyl-3-(4-methoxyphenyl)propanoate (10.0 g, 42.3 mmol) in dichloromethane (500 mL). The mixture was stirred for 6 hours at −20° C. to −5° C. The reaction mixture was poured into a mixture of ice (600 g) with 3 mol/L hydrochloric acid (400 mL) and the dichloromethane layer was separated, which was washed with water and brine, dried over anhydrous sodium sulfate, and then concentrated. The residue was purified by silica gel column chromatography (eluent n-hexane:ethyl acetate=4:1 v/v) to afford 10.9 g (97%) of the title compound as a light brown oily product.

Mass analysis m/z 264 ($M^+$).

EXAMPLE 107

Ethyl 2-ethyl-3-[3-(hydroxyimino)-4-methoxyphenyl]propanoate

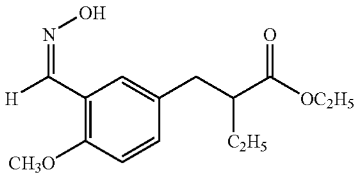

A mixture of ethyl 2-ethyl-3-(3-formyl-4-methoxyphenyl)propanoate (1.06 g, 4.01 mmol), hydroxylamine hydrochloride (293 mg, 4.22 mmol), pyridine (1 mL) and ethanol (20 mL) was refluxed for 6 hours. After cooling, the mixture was concentrated and the residue was dissolved in ethyl acetate, which was washed with 1 mol/L hydrochloric acid, saturated aqueous solution of sodium hydrogencarbonate and brine, dried over anhydrous sodium sulfate, and then concentrated. The residue was purified by silica gel column chromatography (eluent: n-hexane:ethyl acetate=6:1 v/v) to afford 1.00 g (89%) of the title compound as a pale yellow oil.

Mass analysis m/z 279 ($M^+$).

EXAMPLE 108

Ethyl 3-[3-(aminomethyl)-4-methoxyphenyl]-2-ethyl-propanoate hydrochloride

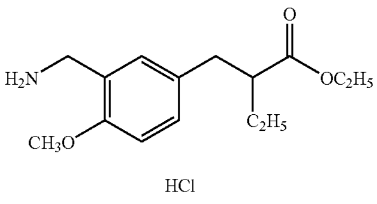

To a solution of ethyl 2-ethyl-3-[3-(hydroxyimino)-4-methoxyphenyl]propanoate (1.00 g, 3.58 mmol) in ethanol (80 mL), 10% palladium on carbon (500 mg) and concentrated hydrochloric acid (4 mL) were added and hydrogenation was performed for 2 hours at room temperature under a hydrogen pressure of 392 kPa. After water (80 mL) was added to the reaction mixture, the catalyst was removed by filtration, which was washed with 50% water-containing ethanol. The filtrate was concentrated and the residue obtained was suspended into diethyl ether (20 mL). The crystals were collected by filtration, washed with diethyl ether, and then dried to afford 914 mg (85%) of the title compound as colorless crystals.

Mass analysis m/z 265 ($M^+$).

EXAMPLE 109

Ethyl 2-ethyl-3-[3-[4-(trifluoromethyl)benzoylaminomethyl]-4-methoxyphenyl]propanoate

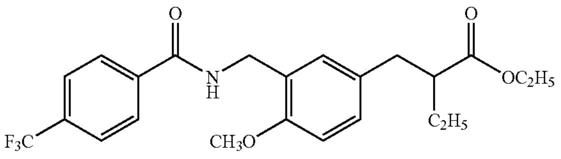

To a solution of 4-(trifluoromethyl)benzoic acid (114 mg, 0.600 mmol) and triethylamine (0.21 mL, 1.51 mmol) in dichloromethane (3 mL), ethyl chlorocarbonate (0.063 mL, 0.659 mmol) was added under stirring and cooling with ice, and the mixture was stirred for 20 minutes. Next, after ethyl 2-ethyl-3-[3-(aminomethyl)-4-methoxyphenyl]propanoate hydrochloride (200 mg, 0.663 mmol) was added, the mixture was stirred for 1 hour under cooling with ice and for 3 hours at room temperature. Dichloromethane (20 mL) was added to the reaction mixture, which was washed with 1 mol/L hydrochloric acid, saturated aqueous solution of sodium hydrogencarbonate and brine, dried over anhydrous sodium sulfate, and then concentrated. The residue was purified by silica gel column chromatography (eluent: n-hexane:ethyl acetate=4:1 v/v) to afford 245 mg (93%) of the title compound as colorless crystals.

Mass analysis m/z 437 ($M^+$).

EXAMPLES 110 AND 111

Similarly to Example 109, compounds in Table 6 were obtained.

TABLE 6

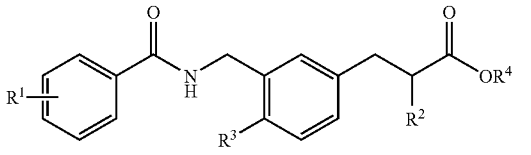

| Example | $R^1$ | $R^2$ | $R^3$ | $R^4$ | Mass analysis (m/z) |
|---|---|---|---|---|---|
| 110 | 4-OPh | $C_2H_5$ | $OCH_3$ | $C_2H_5$ | 461 ($M^+$) |
| 111 | 4-OPh(4-F) | $C_2H_5$ | $OCH_3$ | $C_2H_5$ | 479 ($M^+$) |

EXAMPLE 112

2-Ethyl-3-[3-[4-(trifluoromethyl)benzoylamino-methyl]-4-methoxyphenyl]propanoic acid

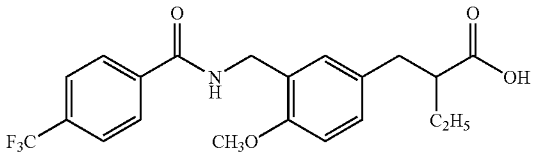

A mixture of ethyl 2-ethyl-3-[3-[4-(trifluoromethyl)benzoylaminomethyl] -4-methoxyphenyl]propanoate (240 mg, 0.549 mmol), methanol (6 mL) and 2.5 mol/L aqueous solution of sodium hydroxide (2 mL) was stirred for 4 hours under heating at 50° C. After cooling, water (20 mL) was added and the mixture was made acidic with 1 mol/L hydrochloric acid, which was then extracted with ethyl acetate. The organic later was washed with water and brine, dried over anhydrous sodium sulfate, and then concentrated to afford 222 mg (99%) of the title compound as colorless crystals. Further, these were recrystallized from diethyl ether-n-hexane, thus affording 161 mg (72%) of purified title compound as colorless needles.

Melting point 132–1330° C. Mass analysis m/z 409 ($M^+$). Elemental analysis C21H22F3NO4 (409.40): Calc. (%) C, 61.61; H, 5.42; N, 3.42. Found (%) C, 61.70; H, 5.56; N, 3.47. $^1$H-NMR (400 MHz, $CDCl_3$) δ0.95 (3H, t, J=7.3 Hz), 1.54–1.70 (2H, m), 2.51–2.59 (1H, m), 2.71 (1H, dd, J=13.7, 6.3Hz), 2.88 (1H, dd, J=13.7, 8.3 Hz), 3.85 (3H, s), 4.58 (2H, d, J=5.9 Hz), 6.78–6.82 (2H, m), 7.10 (1H, dd, J=8.3, 2.4 Hz), 7.16 (1H, d, J=2.4 Hz), 7.65 (2H, d, J=8.3 Hz), 7.85 (2H, d, J=8.3 Hz).

EXAMPLES 113 AND 114

Similarly to Example 112, compounds shown in Table 7 were synthesized.

TABLE 7

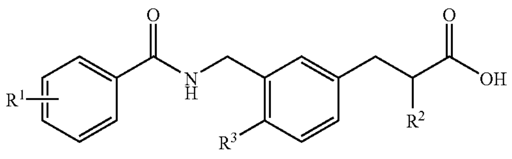

| Example | $R^1$ | $R^2$ | $R^3$ | Melting point(° C.) | Charac. formula | Elemental analysis(%) |
|---|---|---|---|---|---|---|
| 113 | 4-OPh | H | $OCH_3$ | 103–104 | $C_{26}H_{27}NO_5$ | Calc.; C 72.04, H 6.28, N 3.23<br>Found; C 71.67, H 6.24, N 3.37 |

TABLE 7-continued

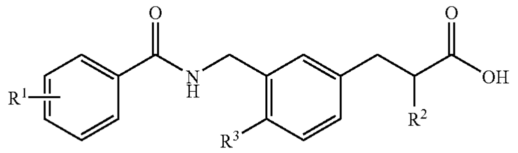

| Example | $R^1$ | $R^2$ | $R^3$ | Melting point(° C.) | Charac. formula | Elemental analysis(%) |
|---|---|---|---|---|---|---|
| 114 | 4-OPh(4-F) | H | $OCH_3$ | 126–128 | $C_{26}H_{26}FNO_5$ | Calc.; C 69.17, H 5.80, N 3.10<br>Found; C 68.91, H 5.80, N 3.13 |

EXAMPLE 115

Ethyl-2-ethyl-3-[3-[4-(trifluoromethyl)benzylaminomethyl]-4-methoxyphenyl]propanoate

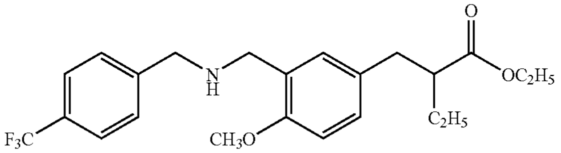

To a solution of ethyl 3-[3-(aminomethyl)-4-methoxyphenyl]-2-ethylpropanoate hydrochloride (203 mg, 0.673 mmol) in N,N-dimethylformamide (4 mL), potassium carbonate (232 mg, 1.68 mmol) and 4-(trifluoromethyl)benzyl bromide (169 mg, 0.707 mmol) were added, and then the mixture was stirred for 3 hours at room temperature and for 4 hours under heating at 60° C. After cooling, the mixture was poured in ice water, which was extracted with diethyl ether. The organic later was washed with water and brine, dried over anhydrous sodium sulfate, and then concentrated. The residue was purified by silica gel column chromatography (eluent: n-hexane:ethyl acetate=2:1 v/v) to afford 92.3 mg (32%) of the title compound as a colorless oil.

Mass analysis m/z 424 (M+H).

EXAMPLE 116

2-Ethyl 3-[3-[4-(trifluoromethyl)benzylamino-methyl]-4-methoxyphenyl]propanoic acid hydrochloride

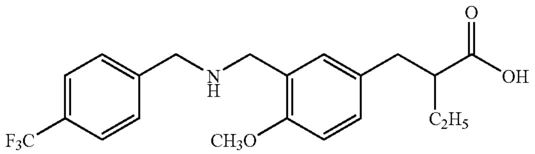

HCl

A mixture of ethyl 2-ethyl-3-[3-[4-(trifluoromethyl)benzylaminomethyl]-4-methoxyphenyl]propanoate (90.2 mg, 0.213 mmol), methanol (2 mL) and 2.5 mol/L aqueous solution of sodium hydroxide (2 mL) was stirred for 5 hours under heating at 60° C. After cooling, ice water (20 mL) was added and the mixture was made acidic with 1 mol/L hydrochloric acid, which was then saturated with sodium chloride and extracted with ethyl acetate. The extracte was washed with saturated brine, dried over anhydrous sodium sulfate, and then concentrated. The residue was purified by silica gel column chromatography (eluent: dichloromethane: methanol=10:1 v/v) to afford 78.0 mg (85%) of the title compound as a brown oil.

Mass analysis As $C_{21}H_{24}F_3NO_3$, m/z 394 $(M-1)^+$. Elemental analysis $C_{21}H_{24}F_3NO_3$.HCl (431.88): Calc. (%) C, 58.40; H, 5.83; N, 3.24. Found (%) C, 58.48; H, 6.07; N, 3.03. $^1$H-NMR (400 MHz, $CDCl_3$) δ0.99 (3H, t, J=7.3 Hz), 1.54–1.61 (1H, m), 1.71–1.78 (1H, m), 2.52–2.57 (1H, m), 2.71–2.83 (2H, m), 3.72 (3H, s), 3.88–3.98 (4H, m), 6.67 (1H, d, J=8.8 Hz), 7.10 (1H, dd, J=2.0, 8.8 Hz), 7.30 (1H, d, J=2.0 Hz), 7.63 (2H, d, J=8.3 Hz), 7.71 (2H, d, J=8.3 Hz).

EXAMPLE 117

4-Methoxy-3-[2-[4-(trifluoromethyl)phenyl]ethoxy]benzaldehyde

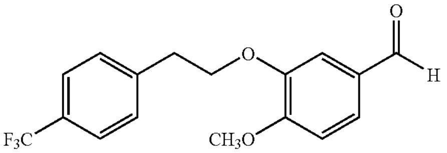

Under an argon atmosphere, stirring and cooling with ice, diethyl azodicarboxylate (40% toluene solution, 3.80 mL, 8.38 mmol) was added dropwise to a solution of 2-[4-(trifluoromethyl)phenyl]ethanol (1.59 g, 8.36 mmol), isovanillin (1.28 g, 8.41 mmol) and triphenylphosphine (2.20 g, 8.39 mmol) in anhydrous tetrahydrofuran (50 mL). After completion of the dropwise addition, the mixture was stirred for 1 hour under cooling with ice, and then allowed to stand overnight at room temperature. The reaction mixture was concentrated and the residue was purified by silica gel column chro-matography (eluent: n-hexane:ethyl acetate=6:1 v/v) to afford 1.96 g (72%) of the title compound as colorless crystals.

Mass analysis m/z 324 $(M^+)$.

EXAMPLE 118

Ethyl 2-ethyl-3-[4-methoxy-3-[2-[4-(trifluoromethyl)phenyl]ethoxy]phenyl]acrylate

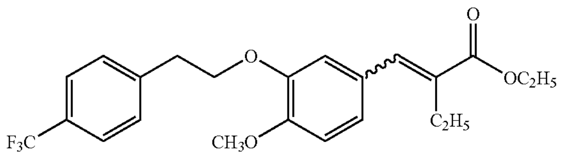

Under an argon atmosphere, stirring and cooling with ice, a solution of triethyl 2-phosphonobutyrate (555 mg, 2.20 mmol) in anhydrous tetrahydrofuran (5 mL) was added dropwise to a solution of potassium tert-butoxide (250 mg, 2.23 mmol) in anhydrous tetrahydrofuran (10 mL), and then the mixture was stirred for 20 minutes. Following this, a solution of 4-methoxy-3-[2-[4-(trifluoromethyl)phenyl]ethoxy]benzaldehyde (650 mg, 2.00 mmol) in anhydrous tetrahydrofuran (5 mL) was added dropwise and then the mixture was stirred for 1 hour under cooling with ice and for 4 hours at room temperature. Cooled 0.5 mol/L hydrochloric acid (30 mL) was added to the reaction mixture, which was extracted with ethyl acetate. The organic layer was washed with water and brine, dried over anhydrous sodium sulfate, and then concentrated. The residue was purified by silica gel column chromatography (eluent: n-hexane:ethyl acetate=6:1 v/v) to afford 842 mg (99%) of the title compound as a colorless oily product.

Mass analysis m/z 422 ($M^+$).

EXAMPLE 119

Ethyl 2-ethyl-3-[4-methoxy-3-[2-[4-(trifluoromethyl)phenyl]ethoxy]phenyl]propanoate

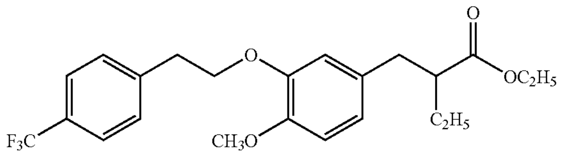

Ethyl 2-ethyl-3-[4-methoxy-3-[2-[4-(trifluoromethyl)phenyl]ethoxy]phenyl]acrylate (840 mg, 1.99 mmol), 5% palladium on carbon (100 mg) and ethyl acetate (50 mL) were mixed, and hydrogenation was carried out for 6 hours at room temperature. The catalyst was removed by filtration, and then the filtrate was concentrated to afford 803 mg (95%) of the title compound as colorless crystals.

Mass analysis m/z 424 ($M^+$).

EXAMPLE 120

2-Ethyl-3-[4-methoxy-3-[2-[4-(trifluoromethyl)phenyl]ethoxy]phenyl]propanoic acid

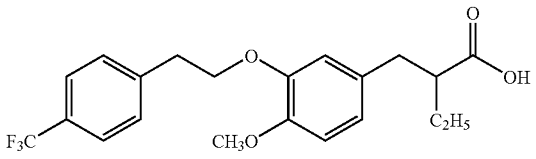

A mixture of ethyl 2-ethyl-3-[4-methoxy-3-[2-[4-(trifluoromethyl)phenyl]ethoxy]phenyl]propanoate (793 mg, 1.87 mmol), methanol (20 mL) and 1 mol/L aqueous solution of sodium hydroxide (10 mL) was stirred for 4 hours at 60° C. After cooling, ice water (50 mL) was added and the mixture was made acidic with 1 mol/L hydrochloric acid, which was then extracted with ethyl acetate. The organic layer was washed with water and brine, dried over anhydrous sodium sulfate, and then concentrated. The residue was purified by silica gel column chromatography (eluent: n-hexane:ethyl acetate=4:1 v/v) to afford 654 mg (88%) of the title compound as colorless crystals. Further, these were recrystallized from diethyl ether-n-hexane, thus obtaining 391 mg of the purified title compound as colorless needles.

Melting point 64–66° C. Mass analysis m/z 396 (M+). Elemental analysis $C_{21}H_{23}F_3O_4$ (396.40): Calc. (%) C, 63.63; H, 5.85. Found (%) C, 63.66; H, 5.80. $^1$H-NMR (400 MHz, $CDCl_3$) δ0.93 (3H, t, J=7.3 Hz), 1.51–1.68 (2H, m), 2.51–2.58 (1H, m), 2.66 (1H, dd, J=13.7, 6.8 Hz), 2.87 (1H, dd, J=13.7, 7.8 Hz), 3.18 (2H, t, J=7.3 Hz), 3.82 (3H, s), 4.20 (2H, t, J=7.3 Hz), 6.68 (1H, d, J=2.0 Hz), 6.73 (1H, dd, J=7.8, 2.0 Hz), 6.79 (1H, d, J=8.3 Hz), 7.41 (2H, d, J=8.3 Hz), 7.56 (2H, d, J=8.3 Hz).

EXAMPLE 121

(+)-2-Ethyl-3-[4-methoxy-3-[[N-[4-(trifluoromethyl)phenyl]carbamoyl]methyl]phenyl]propanoic acid and (−)-2-ethyl-3-[4-methoxy-3-[[N-[4-(trifluoromethyl)phenyl]methyl]carbamoyl]phenyl]propanoic acid (±)-2-Ethyl-3-[4-methoxy-3-[[N-[4-(trifluoromethyl)phenyl]carbamoyl]methyl]phenyl]propanoic acid (compound in Example 88: 14.2 g, 34.7 mmol) and dehydrated tetrahydrofuran (100 mL) were mixed under an argon atmosphere, and triethylamine (4.86 ml, 35.0 mmol) and pivaloyl chloride (4.27 mL, 34.7 mmol) were added dropwise under stirring and cooling with ice. Thereafter, the mixture was stirred for 1 hour at room temperature to synthesize mixed acid anhydride. On the other hand, potassium tert-butoxide (4.67 g, 41.6 mmol) and dehydrated tetrahydrofuran (45 mL) were mixed under cooling with ice and argon atmosphere in another vassel, and (S)-4-benzyl-oxazolidine-2-one (7.38 g, 41.6 mmol) dissolved into dehydrated tetrahydrofuran (60 mL) was added dropwise. After completion of the dropwise addition, the mixture was stirred for 30 minutes. Next, a suspension of the mixed acid anhydride synthesized previously was added dropwise while filtering under an atmosphere of argon. After completion of the drop-wise addition, the reaction mixture was concentrated and then poured in water, which was extracted with ethyl acetate. The extracte was washed with 5% hydrochloric acid, saturated aqueous solution of sodium hydrogencarbonate and brine, then dried over anhydrous magnesium sulfate, and concentrated. The residue was purified by means of silica gel column chromatography (eluent: isopropyl ether) to afford 2.65 g (13%) of (4S)-3-[2-ethyl-3-[4-methoxy-3-[[N-[4-(trifluoromethyl)phenyl]carbamoyl]methyl]phenyl]-propanoyl]-4-benzyloxazolidine-2-one with high polarity as a oily product. Also, 3.84 g (20%) of (4S)-3-[2-ethyl-3-[4-methoxy-3-[[N-[4-(trifluoromethyl)phenyl]carbamoyl]-methyl]phenyl]propanoyl]-4-benzyloxazolidine-2-one with low polarity were obtained by purifying by silica gel column chromatography, followed by further recrystallization from a mixed solvent of n-hexane with isopropyl ether, as colorless powder.

The (4S)-3-[2-ethyl-3-[4-methoxy-3-[[N-[4-(trifluoromethyl)phenyl]carbamoyl]methyl]phenyl]propanoyl]-4-benzyloxazolidine- 2-one with high polarity (2.65 g, 4.66 mmol) was dissolved into a mixed solvent (4:1 v/v) (23 mL) of tetrahydrofuran with water, and cooled with ice after replacement with argon. Under stirring, 30% aqueous hydrogen peroxide (1.89 mL, 18.6 mmol) was added dropwise over 5 minutes. Following this, lithium hydroxide monohydrate (313 mg, 7.46 mmol) dissolved into water (7.8 mL) was added dropwise over 5 minutes, and the mixture was stirred further for 4 hours under cooling with ice. To the reaction mixture, 64% sodium hydrogensulfite (2.98 g, 18.6 mmol) dissolved into water (12 mL) was added dropwise. The reaction mixture was concentrated and the residue was poured into ice water, which was made acidic by adding 5% hydrochloric acid, and then extracted with methylene chloride. The extracte was washed with brine, then dried over anhydrous magnesium sulfate and concentrated. The residue was dissolved into isopropyl ether under heating and allowed to stand. The precipitated crystals were collected by filtration and dried. Further, after concentration, the filtrate was purified by silica gel column chromatography (eluent: methylene chloride:methanol=20:1→15:1 v/v) to afford 1.37 g (72%) of (+)-2-ethyl-3-[4-methoxy-3-[[N-[4-(trifluoromethyl)-phenyl]carbamoyl]methyl]phenyl]propanoic acid as colorless crystalline powder.

Melting point 119–120° C. Mass analysis m/z 409 ($M^+$). Elemental analysis (%) $C_{21}H_{22}F_3NO_4$ (409.40): Calc. C, 61.61; H, 5.42; N, 3.42. Found C, 61.48; H, 5.46; N, 3.45. $^1$H-NMR (400 MHz, CDCl3) δ0.95 (3H, t, J=7.3 Hz), 1.55–1.70 (2H, m), 2.56–2.61 (1H, m), 2.73 (1H, dd, J=13.7, 6.3 Hz), 2.88 (1H, dd, J=13.7, 8.3 Hz), 3.67 (2H, s), 3.90 (3H, s), 6.86 (1H, d, J=8.8 Hz), 7.11–7.13 (2H, m), 7.50 (2H, d, J=8.8 Hz), 7.53 (2H, d, J=8.8 Hz), 7.93 (1H, br s). Specific rotation $[\alpha]D^{26}$ +21° (C 0.8, MeOH); Optical purity 99% e.e.(Chiral Pak AD 0.0046×0.25 m, eluate; n-hexane:isopropanol:trifluoroacetic acid=95:5:0.2 v/v/v, detecting wavelength; 254 nm, column temperature; 40° C., flow rate; 1.00 mL/min).

On the other hand, using (4S)-3-[2-ethyl-3-[4-methoxy-3-[[N-[4-(trifluoromethyl)phenyl]carbamoyl]methyl]phenyl]-propionyl]-4-benzyloxazolidine-2-one with low polarity (3.84 g, 6.75 mmol), similar manipulation to the hydrolysis of (4S)-3-[2-ethyl-3-[4-methoxy-3-[[N-[4-(trifluoromethyl)phenyl]-carbamoyl]methyl]phenyl]propionyl]-4-benzyloxazolidine-2-one with high polarity was conducted to obtain (−)-2-ethyl-3-[4-methoxy-3-[[N-[4-(trifluoromethyl)phenyl]carbamoyl]methyl]-phenyl] propanoic acid (1.55 g, 56%) as colorless crystalline powder.

Melting point 121–123° C. Mass analysis m/z 409 ($M^+$). Elemental analysis (%) $C_{21}H_{22}F_3NO_4$ (409.40): Calc. C, 61.61; H, 5.42; N, 3.42. Found C, 61.51; H, 5.47; N, 3.50.

$^1$H-NMR (400 MHz, CDCl3) δ0.95 (3H, t, J=7.3 Hz), 1.55–1.70 (2H, m), 2.55–2.61 (1H, m), 2.73 (1H, dd, J=13.7, 6.4 Hz), 2.88 (1H, dd, J=13.7, 8.3 Hz), 3.67 (2H, s), 3.91 (3H, s), 6.86 (1H, d, J=8.3 Hz), 7.11–7.13 (2H, m), 7.50 (2H, d, J=8.8 Hz), 7.54 (2H, d, J=8.8 Hz), 7.91 (1H, br s). Specific rotation $[\alpha]D^{26}$ −22° (C 0.8, MeOH); Optical purity 98% e.e. (Chiral Pak AD 0.0046×0.25 m, eluate; n-hexane:isopropanol:trifluoroacetic acid=95:5:0.2 v/v/v, detecting wavelength; 254 nm, column temperature; 40° C., flow rate; 1.00 mL/min).

EXAMPLE 122

(4-Methoxy-3-nitrophenyl)methanol

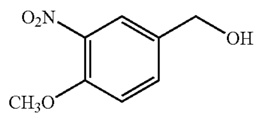

Under an argon atmosphere and cooling with ice, borane-tetrahydrofuran complex (1.00 mol/L, tetrahydrofuran solution, 100 mL, 100 mmol) was added dropwise to a solution of 4-methoxy-3-nitrobenzoic acid (15.3 g, 76.1 mmol) in anhydrous tetrahydrofuran (200 mL) under stirring. After completion of the dropwise addition, the mixture was allowed to stand overnight at room temperature. The reaction mixture was cooled with ice again and 6 mol/L hydrochloric acid (20 mL) was added dropwise. After stirring for 30 minutes, the mixture was concentrated under reduced pressure. The residue was poured into 1 L of ice water and, after stirring for 30 minutes, the precipitates produced were collected by filtration, washed with water and dried to afford 12.5 g (90%) of the title compound as pale yellow crystals.

Mass analysis m/z 183 ($M^+$).

EXAMPLE 123

4-(Bromomethyl)-2-nitroanisole

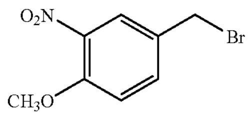

Under an argon atmosphere and cooling with ice, phosphorus tribromide (2.36 mL, 24.7 mmol) was added dropwise to a solution of (4-methoxy-3-nitrophenyl)methanol (12.2 g, 66.6 mmol) in anhydrous ether (350 mL) under stirring, and the mixture was stirred for 3.5 hours. Ice water (300 mL) was added to the reaction mixture. The organic layer was separated, washed with water and brine, dried over anhydrous sodium sulfate, and then concentrated. The residue was purified by means of silica gel column chromatography (eluent: n-hexane:ethyl acetate=2:1→1:1 v/v) to afford 8.36 g (51%) of the title compound as pale yellow crystals.

Mass analysis m/z 245 ($M^+$)

EXAMPLE 124

[3(2S),4R]-3-[2-ethyl-3-(4-methoxy-3-nitrophenyl) propionyl]-4-benzyloxazolidine-2-one

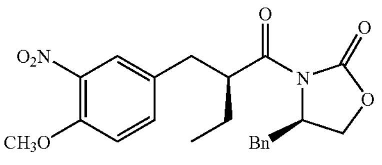

Under an argon atmosphere, sodium bis(trimethylsilyl)-amide (1.0 mol/L tetrahydrofuran solution, 11.1 mL, 11.1 mmol) was added dropwise to a solution of (R)-3-(1-butyryl)-4-benzyloxazolidine-2-one (2.47 g, 9.99 mmol) in anhydrous tetrahydrofuran (50 mL) at −78° C. under stirring, and then the mixture was stirred for 1 hour. Following this, a solution of 4-(bromomethyl)-2-nitroanisole (2.72 g, 11.1 mmol) in anhydrous tetrahydrofuran (30 mL) was added dropwise, and the mixture was stirred for 4 hours at a temperature from −78° C. to −60° C. Saturated aqueous solution of ammonium chloride (100 mL) was added, which was extracted with ethyl acetate. The extracted solution was washed with water and brine, then dried over anhydrous sodium sulfate and concentrated. The residue was purified by silica gel column chromatography (eluent n-hexane:ethyl acetate=4:1→2:1 v/v) to afford 3.40 g (82%) of the title compound as pale yellow crystals.

Mass analysis m/z 412 ($M^+$).

EXAMPLE 125

[3(2S),4R]-3-[2-ethyl-3-(3-amino-4-methoxyphenyl) propanoyl]-4-benzyloxazolidine-2-one

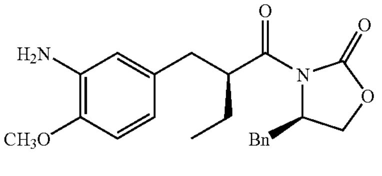

To [3(2S),4R]-3-[2-ethyl-3-(4-methoxy-3-nitrophenyl)-propanoyl]-4-benzyloxazolidine-2-one (3.39 g, 8.22 mmol), a mixed solvent (100 mL) of tetrahydrofuran with ethanol (1:1 v/v) and 10% palladium on carbon (0.34 g) were added, and the mixture was stirred for 7.5 hours at room temperature under a hydrogen pressure of 294 kPa. The catalyst was removed by filtration and the filtrate was concentrated to afford the title compound quantitatively as a yellowish brown amorphous material.

Mass analysis m/z 382 ($M^+$)

EXAMPLE 126

[3(2s),4R]-3-[2-ethyl-3-[4-methoxy-3-[2-[4-(trifluoromethyl)phenyl]acetylamino]phenyl]propanoyl]-4-benzyloxazolidine-2-one

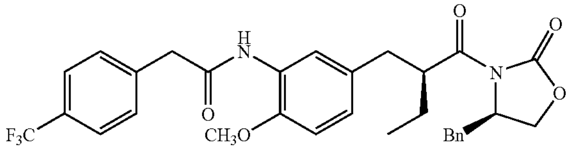

To a solution of 4-(trifluoromethyl)phenylacetic acid (0.889 g, 4.22 mmol) and [3(2S),4R]-3-[2-ethyl-3-(3-amino-4-methoxyphenyl)propanoyl]-4-benzyloxazolidine-2-one (1.11 g, 2.82 mmol) in dichloromethane (25 mL), N-cyclohexylcarbodiimide-N' -methyl polystyrene HL (1.65 mmol/g; 3.84 g, 6.34 mmol) was added, and the mixture was stirred for 7 hours at room temperature. The insolubles were removed by filtration and the filtrate was concentrated. The residue was purified by silica gel column chromatography (eluent: n-hexane:ethyl acetate=2:1 v/v) to afford 1.57 g (98%) of the title compound as a pale yellow amorphous material.

Mass analysis m/z 568 ($M^+$)

EXAMPLE 127

(S)-(+)-2-ethyl-3-[4-methoxy-3-[2-[4-(trifluoromethyl)phenyl]acetylamino]phenyl]propanoic acid

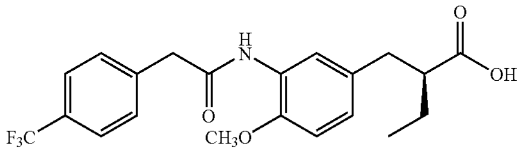

To a solution of [3((2S),4R]-3-[2-ethyl-3-[4-methoxy-3-[2-[4-(trifluoromethyl)phenyl]acetylamino]phenyl]propanoyl]-4-benzyloxazolidine-2-one (1.55 g, 2.73 mmol) in tetrahydrofuranethanol (4:1) (15 mL), 30% aqueous hydrogen peroxide (1.11 mL, 11.0 mmol) and successively aqueous solution of lithium hydroxide monohydrate (5 mL) were added dropwise under stirring and cooling with ice. After stirring for 3.5 hours, an aqueous solution of sodium hydrogensulfite (7 mL) was added dropwise, the mixture was stirred for 10 minutes, and then concentrated. The residue was extracted with ethyl acetate, washed with water and brine, then dried over anhydrous sodium sulfate and concentrated. The residue was purified by column chromatography (eluent: methanol→mixed solvent of methanol with 1 mol/L hydrochloric acid (9:1) that uses ion exchange resin (Amberlite IRA410) and silica gel column chromatography (eluent: n-hexane:ethyl acetate=2:1→1:2 v/v) to afford 672 mg (60%) of the title compound as a pale yellow amorphous material.

Mass analysis m/z 409 ($M^+$). Elemental analysis $C_{21}H_{22}F_3NO_4$ (409.40): Calcd. (%) C, 61.61; H, 5.42; N, 3.42. Found (%) C, 61.39; H, 5.42; N, 3.46. $^1$H-NMR (400 MHz, $CDCl_3$) δ0.93 (3H, t, J=7.3 Hz), 1.50–1.69 (2H, m), 2.55–2.64 (1H, m), 2.69 (1H, dd, J=13.7, 6.8 Hz), 2.90 (1H, dd, J=13.7, 7.8 Hz), 3.74 (3H, s), 3.79 (3H, s), 6.72 (1H, d, J=8.3 Hz), 6.84 (1H, dd, J=8.3, 2.0 Hz), 7.47 (2H, d, J=8.3 Hz), 7.64 (2H, d, J=8.3 Hz), 7.75 (1H, br s), 8.21 (1H, d, J=2.0 Hz). Specific rotation [α]D[26] +30° (C 0.80, MeCN); Optical purity 99% e.e. (Chiralcel OJ, 0.0046×0.25 m, eluate; n-hexane:isopropanol:trifluoroacetic acid=95:5:0.2, detecting wave-length; 254 nm, column temperature; 40° C., flow rate; 1.00 ml/min).

(Biological Activity)

TEST EXAMPLE 1

Test of Transcriptional Activation on Peroxisome Proliferator-Activated Receptor α

To CHO cells cultured in a Dulbecco-modified Eagle's medium containing 10% delipid fetal calf serum (FCS/DMEM), receptor plasmid that expresses fused protein of DNA-binding domain being transcription factor of yeast with ligand-binding domain of human type PPARα (Biochemistry, 1993, 32, 5598), its reporter plasmid (STRATAGENE Corp.) and luciferase plasmid of Renilla (Promega Corp.) as internal standard were cotransfected with lipofectamine in the serum-free state. Thereafter, testing compound was added in the 10% SFCS/DMEM and both luciferase activities were measured after 24 hours, which were corrected with internal standard.

Results are shown in Table 8. From these results, it was shown that the inventive compounds had potent transcriptional activity on human peroxisome prolifertor-activated receptor α.

TABLE 8

| Example | Transcription-activating function EC50 (μmol/L) |
|---|---|
| 44 | 0.13 |
| 46 | 0.05 |
| 70 | 0.16 |
| 88 | 0.015 |
| (8S) HETE | 1.30 |

<Result>

From the results as described above, the inventive substituted phenylpropionic acid derivatives are novel compounds group with excellent binding activity to PPARα and transcriptional activation.

Based on the fact that these inventive compounds have potent working activity on PPARα, it can be said that they are effective compounds as lipid-decreasing drugs aforementioned, in particular, lipid-decreasing drugs for liver, and suppressing drugs for the progress of arterial sclerosis.

The invention claimed is:

1. A substituted phenylpropionic acid derivative represented by the formula (1):

(1)

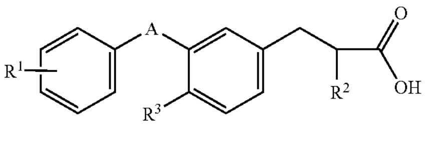

wherein $R^1$ represents a lower alkyl group of 1 to 4 carbon atoms, lower alkoxy group having 1 to 3 carbon atoms, trifluoromethyl group, trifluoromethoxy group, phenyl group which is unsubstituted or substituted with at least one lower alkyl group of 1 to 4 carbon atoms or a lower alkoxy group of 1 to 3 carbon atoms, phenoxy group which is unsubstituted or substituted with at least one lower alkyl group of 1 to 4 carbon atoms or a lower alkoxy group of 1 to 3 carbon atoms or benzyloxy group which is unsubstituted or substituted with at least one lower alkyl group of 1 to 4 carbon atoms or a lower alkoxy group of 1 to 3 carbon atoms, $R^2$ represents a hydrogen atom, lower alkyl group of 1 to 4 carbon atoms or lower alkoxy group of 1 to 3 carbon atoms, $R^3$ represents a lower alkoxy group of 1 to 3 carbon atoms, and

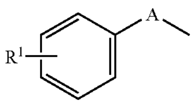

represents

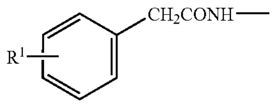

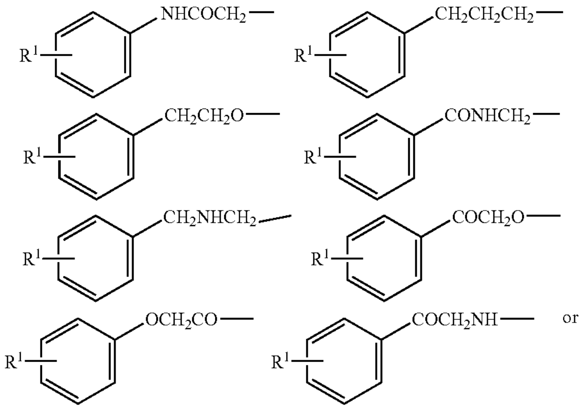

or

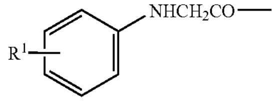

and pharmaceutically acceptable salts and hydrates thereof.

2. The substituted phenylpropionic acid derivative and pharmaceutically acceptable salt and hydrate thereof of claim 1, which is represented by formula (1a):

(1a)

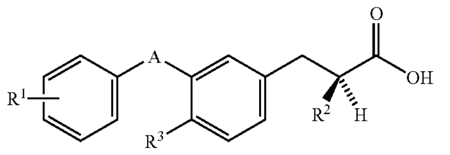

wherein $R^1$, $R^2$ and $R^3$ are as defined in claim 1.

3. The substituted phenylpropionic acid derivative and pharmaceutically acceptable salts and hydrate thereof of claim 1, wherein $R^1$ is a trifluoromethyl group.

4. The substituted phenylpropionic acid derivative and pharmaceutically acceptable salt and hydrate thereof of claim 1, wherein $R^1$ is a benzyloxy group.

5. The substituted phenylpropionic acid derivative and pharmaceutically acceptable salt and hydrate thereof of claim 1, wherein $R^1$ is a phenoxy group.

6. The substituted phenylpropionic acid derivative and pharmaceutically acceptable salt and hydrate thereof of claim 1, wherein $R^1$ is a 4-fluorophenoxy group.

7. The substituted phenylpropionic acid derivative and pharmaceutically acceptable salt and hydrate thereof of claim 1, wherein $R^2$ is an ethyl group.

8. The substituted phenylpropionic acid derivative and pharmaceutically acceptable salt and hydrate thereof of claim 1, wherein $R^2$ is a n-propyl group.

9. The substituted phenylpropionic acid derivative and pharmaceutically acceptable salt and hydrate thereof of claim 1, wherein $R^2$ is a methoxy group.

10. The substituted phenylpropionic acid derivative and pharmaceutically acceptable salt and hydrate thereof of claim 1, wherein -A- represents —$CH_2CONH$—.

11. The substituted phenylpropionic acid derivative and pharmaceutically acceptable salt and hydrate thereof of claim 1, wherein -A- represents —$NHCOCH_2$—.

12. The substituted phenylpropionic acid derivative and pharmaceutically acceptable salt and hydrate thereof of claim 1, wherein -A- represents —$CONHCH_2$—.

13. The substituted phenylpropionic acid derivative and pharmaceutically acceptable salt and hydrate thereof of claim 1, which is 2-ethyl-3-[4-methoxy-3-[2-[4-(tri-fluoromethyl)phenyl]acetylamino]phenyl]propionic acid.

14. The substituted phenylpropionic acid derivative and pharmaceutically acceptable salt and hydrate thereof of claim 1, which is 2-n-propyl-3-[4-methoxy-3-[2-[4-(tri-fluoromethyl)phenyl]acetylamino]phenyl]propionic acid.

15. The substituted phenylpropionic acid derivative and pharmaceutically acceptable salt and hydrate thereof of claim 1, which is 2-ethyl-3-[4-methoxy-3-[2-(4-phenoxy-phenyl)acetylamino]phenyl]propionic acid.

16. The substituted phenylpropionic acid derivative and pharmaceutically acceptable salt and hydrate thereof of claim 1, which is 2-n-propyl-3-[4-methoxy-3-[2-(4-phenoxy-phenyl)acetylamino]phenyl]propionic acid.

17. The substituted phenylpropionic acid derivative and pharmaceutically acceptable salt and hydrate thereof of claim 1, which is 2-ethyl-3-[4-methoxy-3-[2-[4-(4-fluoro-phenoxy)phenyl]acetylamino]phenyl]propionic acid.

18. The substituted phenylpropionic acid derivative and pharmaceutically acceptable salt and hydrate thereof of claim 1, which is 2-n-propyl-3-[4-methoxy-3-[2-[4-(4-fluorophenoxy)phenyl]acetylamino]phenyl]propionic acid.

19. The substituted phenylpropionic acid derivative and pharmaceutically acceptable salt and hydrate thereof of claim 1, which is 2-ethyl-3-[4-methoxy-3-[[N-[4-(tri-fluoromethyl)phenyl]carbamoyl]methyl]phenyl]propionic acid.

20. The substituted phenylpropionic acid derivative and pharmaceutically acceptable salt and hydrate thereof of claim 1, which is 2-n-propyl-3-[4-methoxy-3-[[N-[4-(tri-fluoromethyl)phenyl]carbamoyl]methyl]phenyl]propionic acid.

21. The substituted phenylpropionic acid derivative and pharmaceutically acceptable salt and hydrate thereof of claim 1, which is 2-ethyl-3-[4-methoxy-3-[[N-(4-phenoxy-phenyl)carbamoyl]methyl]phenyl]propionic acid.

22. The substituted phenylpropionic acid derivative and pharmaceutically acceptable salt and hydrate thereof of claim 1, which is 2-n-propyl-3-[4-methoxy-3-[[N-(4-phenoxy-phenyl)carbamoyl]methyl]phenyl]propionic acid.

23. The substituted phenylpropionic acid derivative and pharmaceutically acceptable salt and hydrate thereof of claim 1, which is 2-ethyl-3-[4-methoxy-3-[[N-[4-(4-fluoro-phenoxy)phenyl]carbamoyl]methyl]phenyl]propionic acid.

24. The substituted phenylpropionic acid derivative and pharmaceutically acceptable salt and hydrate thereof of claim 1, which is 2-n-propyl-3-[4-methoxy-3-[[N-[4-(4-fluorophenoxy)phenyl]carbamoyl]methyl]phenyl]propionic acid.

25. The substituted phenylpropionic acid derivative and pharmaceutically acceptable salt and hydrate thereof of claim 1, which is 2-ethyl-3-[3-[4-(trifluoromethyl)-benzoylaminomethyl]-4-methoxyphenyl]propionic acid.

26. The substituted phenylpropionic acid derivative and pharmaceutically acceptable salt and hydrate thereof of claim 1, which is 2-ethyl-3-[3-[4-(phenoxy)benzoylamino-methyl]-4-methoxyphenyl]propionic acid.

27. The substituted phenylpropionic acid derivative and pharmaceutically acceptable salt and hydrate thereof of claim 1, which is 2-ethyl-3-[3-[4-(4-fluorophenoxy)-benzoylaminomethyl]-4-methoxyphenyl]propionic acid.

28. A pharmaceutical composition, comprising at least one substituted phenylpropionic acid derivative and pharmaceutically acceptable salt and hydrate thereof of claim 1.

29. A method of treating hyperlipidemia, comprising administering an effective amount of at least one substituted phenylpropionic acid derivative and pharmaceutically acceptable salt and hydrate thereof of claim 1 to a subject.

30. A method of suppressing the progress of arterial sclerosis, comprising administering an effective amount of at least one substituted phenylpropionic acid derivative and pharmaceutically acceptable salt and hydrate thereof of claim 1 to a subject.

31. The pharmaceutical composition of claim 28, which is a solid or liquid composition.

32. The pharmaceutical composition of claim 31, which is a solid in the form of a tablet, pill, capsule, power or granule.

33. The pharmaceutical composition of claim 31, which is a liquid.

34. The pharmaceutical composition of claim 33, which is in the form of an emulsion, syrup, solution, suspension or spray.

* * * * *